United States Patent [19]

Angst et al.

[11] Patent Number: 5,294,734
[45] Date of Patent: Mar. 15, 1994

[54] 4-SUBSTITUTED 2-AMINOALK-3-ENOIC ACIDS

[75] Inventors: Christof Angst, Möhlin, Switzerland; Hans Allgeier, Lörrach-Haagen, Fed. Rep. of Germany; Roland Heckendorn, Arlesheim; Daniel Wallach, Basel, both of Switzerland

[73] Assignee: Ciba-Geigy Corp., Ardsley, N.Y.

[21] Appl. No.: 851,437

[22] Filed: Mar. 16, 1992

Related U.S. Application Data

[63] Continuation-in-part of Ser. No. 586,352, Sep. 21, 1990, abandoned.

[30] Foreign Application Priority Data

Sep. 26, 1989 [CH] Switzerland ............... 3479/89-6

[51] Int. Cl.$^5$ ................ C07F 9/38; A61K 31/66
[52] U.S. Cl. ................... 562/11; 514/114; 560/39; 560/110; 560/169; 560/170
[58] Field of Search ................ 562/11; 514/114; 560/39, 110, 169, 170

[56] References Cited

U.S. PATENT DOCUMENTS

| | | | |
|---|---|---|---|
| 4,399,287 | 8/1983 | Baillie et al. | 548/119 |
| 4,477,391 | 10/1984 | Collins | 562/11 |
| 4,483,853 | 11/1984 | Collins et al. | 424/211 |
| 4,657,899 | 4/1987 | Rzeszotarski et al. | 514/120 |
| 4,761,405 | 8/1988 | Rzeszotarski et al. | 514/114 |
| 4,776,875 | 10/1988 | Löher et al. | 71/86 |
| 4,916,125 | 4/1990 | Herrling et al. | 514/89 |
| 5,051,413 | 9/1991 | Angst et al. | 514/114 |
| 5,095,139 | 3/1992 | Loeffler et al. | 562/11 |
| 5,134,134 | 7/1992 | Allgeier | 514/114 |

FOREIGN PATENT DOCUMENTS

| | | |
|---|---|---|
| 233154 | 2/1986 | European Pat. Off. |
| 0233154 | 8/1987 | European Pat. Off. |
| 0302826 | 7/1988 | European Pat. Off. |
| 391850 | 4/1989 | European Pat. Off. |
| 3609818 | 3/1986 | Fed. Rep. of Germany |
| 53-87314 | 1/1977 | Japan |
| 8706131 | 10/1987 | PCT Int'l Appl. |
| 2104079 | 3/1983 | United Kingdom |

OTHER PUBLICATIONS

Park, et al., "Structure of Plumbemycin A and B, Antagonists of L-Threonine from *Streptomyces plumbeus*"; Agr. Biol. Chem. 41: 573–579 (1977).

Kleinrok, et al., "Preliminary Pharmacological Investigation on 38 Aminophosphonic Acids and Their Derivatives" Pol. J. Pharma. 37:275–284 (1985).

Park, et al., "2-Amino-5-phosphono-3-pentenoic Acid, a New Amino Acid from N-1409 Substance, an Antagonist of Threonine" Agr. Biol. Chem. 40(9):1905–1906 (1976).

*Primary Examiner*—JoséG. Dees
*Assistant Examiner*—B. Frazier
*Attorney, Agent, or Firm*—Irving M. Fishman; Karen G. Kaiser; Barbara J. Ikeler

[57] ABSTRACT

Substituted 2-aminoalk-3-enoic acid derivative of formula I wherein $R_1$ is an aliphatic hydrocarbon radical that is substituted by optionally acylated or aliphatically or araliphatically etherified hydroxy, by halogen, by optionally acylated and/or aliphatically substituted amino or by an aza-, diaza-, azoxa- or oxa-cycloaliphatic radical, or is an oxacycloaliphatic hydrocarbon radical bonded via a carbon atom, or is an optionally aliphatically N-substituted or N-acylated azacycloaliphatic hydrocarbon radical, and $R_2$ is free or esterified carboxy, and their salts exhibit NMDA-antagonistic properties and are useful as active ingredients of anticonvulsive medicaments.

11 Claims, No Drawings

4-SUBSTITUTED 2-AMINOALK-3-ENOIC ACIDS

This is a continuation-in-part of our co-pending U.S. patent application Ser. No. 07/586,352, filed Sep. 21, 1990 now abandoned.

The invention relates to a process for the manufacture of substituted 2-aminoalk-3-enoic acid derivatives of formula I

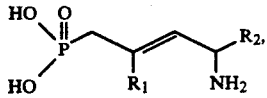

wherein $R_1$ is an aliphatic hydrocarbon radical that is substituted by optionally acylated or aliphatically or araliphatically etherified hydroxy, by halogen, by optionally acylated and/or aliphatically substituted amino or by an aza-, diaza-, azoxa- or oxa-cycloaliphatic radical, or is an oxacycloaliphatic hydrocarbon radical bonded via a carbon atom, or is an optionally aliphatically N-substituted or N-acylated azacycloaliphatic hydrocarbon radical, and $R_2$ is free or esterified carboxy, and of their salt and to a processes for the preparation of pharmaceutical preparations containing them.

Aliphatic hydrocarbon radicals are, for example, alkyl radicals having up to and including 10, especially up to and including 8, carbon atoms, preferably lower alkyl radicals.

Hydroxy-substituted aliphatic hydrocarbon radicals are, for example, mono- or di-hydroxy-lower alkyl.

Acylated hydroxy is, for example, lower alkanoyloxy or benzoyloxy that is unsubstituted or substituted in the phenyl moiety. Accordingly, an aliphatic hydrocarbon radical that is substituted by acylated hydroxy shall be understood as being, for example, lower alkanoyloxy-lower alkyl or benzoyloxy-lower alkyl that is unsubstituted or substituted in the phenyl moiety.

Aliphatically etherified hydroxy is, for example, lower alkoxy; araliphatically etherified hydroxy is, for example, unsubstituted or substituted phenyl-lower alkoxy. Accordingly, an aliphatic hydrocarbon radical that is substituted by aliphatically etherified hydroxy shall be understood as being, for example, lower alkoxy-lower alkyl, and an aliphatic hydrocarbon radical that is substituted by araliphatically etherified hydroxy shall be understood as being, for example, unsubstituted or substituted phenyl-lower alkoxy-lower alkyl.

A halo-substituted aliphatic hydrocarbon radical is, for example, halo-lower alkyl.

Optionally acylated and/or aliphatically substituted amino is, for example, amino, N-mono- or N,N-di-lower alkylamino, N-lower alkanoylamino, N-benzoylamino that is unsubstituted or substituted in the phenyl moiety, or N-lower alkanoyl-N-lower alkylamino. Accordingly, aliphatic hydrocarbon radicals that are substituted by optionally acylated and/or aliphatically substituted amino are, for example, amino-lower alkyl, lower alkylamino-lower alkyl, lower alkanoylamino-lower alkyl, benzoylamino-lower alkyl that is unsubstituted or substituted in the phenyl moiety, di-lower alkylamino-lower alkyl or N-lower alkanoyl-N-lower alkylamino-lower alkyl.

Aliphatic hydrocarbon radicals that are substituted by an azacycloaliphatic radical are, for example, 4- to 7-membered azacycloalkyl-lower alkyl radicals whose azacycloalkyl moiety may be bonded via the N atom or a carbon atom and, in the latter case, may be N-lower alkylated, N-lower alkanoylated or N-substituted by a benzoyl group that is unsubstituted or substituted in the phenyl moiety. 4- to 7-membered azacycloalkyl-lower alkyl whose azacycloalkyl moiety is bonded via the N atom is, for example, N,N-lower alkyleneamino-$C_1$-$C_7$alkyl, i.e. azacycloalk-1-yl-$C_1$-$C_7$alkyl. 4- to 7-membered azacycloalkyl-lower alkyl whose azacycloalkyl moiety is bonded via a carbon atom and is optionally N-lower alkylated, N-lower alkanoylated or N-substituted by a benzoyl group that is unsubstituted or substituted in the phenyl moiety is, for example, 5- to 7-membered azacycloalkyl-$C_1$-$C_7$alkyl or N-$C_2$-$C_7$alkanoylazacycloalkyl-$C_1$-$C_7$alkyl, also N-$C_1$-$C_4$alkylazacycloalkyl-$C_1$-$C_7$alkyl or N-benzoylazacycloalkyl-$C_1$-$C_7$alkyl that is unsubstituted or substituted in the phenyl moiety, each of which is bonded via a carbon atom.

Aliphatic hydrocarbon radicals that are substituted by a diazacycloaliphatic radical are, for example, 4- to 7-membered diazacycloalkyl-lower alkyl radicals whose diazacycloalkyl moiety is bonded via one N atom and may, at the other N atom, optionally be lower alkylated, lower alkanoylated or substituted by a benzoyl group that is unsubstituted or substituted in the phenyl moiety, such as 4- to 7-membered diazacycloalkyl-lower alkyl radicals that are bonded via an N atom and are optionally N'-lower alkylated, N'-lower alkanoylated or N'-substituted by a benzoyl group that is unsubstituted or substituted in the phenyl moiety, especially 5- to 7-membered diazacycloalk-1-yl-$C_1$-$C_7$alkyl.

Aliphatic hydrocarbon radicals that are substituted by an azoxacycloaliphatic radical are, for example, 4- to 7-membered azoxacycloalkyl-lower alkyl radicals whose azoxacycloalkyl moiety is bonded via the N atom, such as 4- to 7-membered azoxacycloalkyl-lower alkyl radicals bonded via the N atom, especially 5- to 7-membered N,N-(oxa-lower alkylene)amino-$C_1$-$C_7$alkyl, i.e. azoxacycloalk-1-yl-$C_1$-$C_7$alkyl.

Aliphatic hydrocarbon radicals that are substituted by an oxacycloaliphatic radical are, for example, 4- to 7-membered oxacycloalkyl-lower alkyl radicals whose oxacycloalkyl moiety is bonded via a carbon atom, such as 5- to 7-membered oxacycloalkyl-$C_1$-$C_7$alkyl bonded via a carbon atom.

Oxacycloaliphatic hydrocarbon radicals that are bonded via a carbon atom are, for example, 5- to 7-membered oxacycloalkyl groups bonded via a carbon atom.

Azacycloaliphatic hydrocarbon radicals that are bonded via a carbon atom and are optionally aliphatically N-substituted or N-acylated are azacycloalkyl radicals that are bonded via a carbon atom and are optionally N-lower alkylated, N-lower alkanoylated or N-substituted by benzoyl that is unsubstituted or substituted in the phenyl moiety, such as 5- to 7-membered azacycloalkyl or N-$C_2$-$C_7$alkanoylazacycloalkyl, also N-$C_1$-$C_4$alkylazacycloalkyl or unsubstituted or substituted N-benzoylazacycloalkyl, each of which is bonded via a carbon atom.

Esterified carboxy is, for example, carboxy esterified by an aliphatic, cycloaliphatic or araliphatic alcohol, such as lower alkoxycarbonyl, 4- up to and including 7-membered, especially 5- or 6-membered, cycloalkoxycarbonyl, such as cyclopentyloxy- or cyclohexyloxycarbonyl, or unsubstituted or substituted phenyl-lower alkoxycarbonyl.

In the groups mentioned above, phenyl radicals may be unsubstituted or mono-, di- or tri-substituted, especially mono- or di-substituted, in customary manner, for example by lower alkyl, lower alkoxy, halogen, cyano and/or by trifluoromethyl.

Hereinbefore and hereinafter, "lower" radicals and compounds shall be understood as being, for example, radicals and compounds containing up to and including 7, preferably up to and including 4, carbon atoms (C atoms).

Lower alkyl is, for example, $C_1$-$C_7$alkyl, preferably $C_1$-$C_4$alkyl, such as methyl, ethyl, propyl, isopropyl or butyl, but may also be isobutyl, sec.-butyl, tert.-butyl or a pentyl, hexyl or heptyl group.

Mono- or di-hydroxy-lower alkyl is, for example, hydroxy-$C_1$-$C_7$alkyl, such as hydroxymethyl, 2-hydroxyethyl, 3-hydroxypropyl, 4-hydroxybutyl, 5-hydroxypentyl or 6-hydroxyhexyl, or dihydroxy-$C_2$-$C_7$alkyl in which the hydroxy groups are bonded to different carbon atoms, such as 1,2-dihydroxyethyl or, especially, 1,3-dihydroxyprop-2-yl.

Lower alkanoyl is, for example, $C_2$-$C_7$alkanoyl, especially $C_2$-$C_4$alkanoyl, such as acetyl, propionyl or butyryl, but may also be a $C_5$-$C_6$alkanoyl group, such as pivaloyl. Accordingly, lower alkanoyloxy-lower alkyl is especially $C_2$-$C_7$alkanoyloxy-$C_1$-$C_7$alkyl, such as acetoxymethyl, propionyloxymethyl, butyryloxymethyl, 2-acetoxyethyl, 3-acetoxypropyl, 4-acetoxybutyl, 5-acetoxypentyl or 6-acetoxyhexyl. By analogy, benzoyloxy-lower alkyl shall be understood as being, for example, benzoyloxy-$C_1$-$C_7$-alkyl that is substituted or substituted in the phenyl moiety, such as benzoyloxymethyl, 2-benzoyloxyethyl, 3-benzoyloxypropyl, 4-benzoyloxybutyl, 5-benzoyloxypentyl or 6-benzoyloxyhexyl.

Lower alkoxy is, for example, $C_1$-$C_7$alkoxy, preferably $C_1$-$C_4$alkoxy, such as methoxy, ethoxy, propoxy, isopropoxy or butoxy, but may also be isobutoxy, sec.-butoxy, tert.-butoxy or a pentyloxy, hexyloxy or heptyloxy group. Accordingly, lower alkoxy-lower alkyl is, for example, $C_1$-$C_4$alkoxy-$C_1$-$C_7$alkyl, such as methoxymethyl, ethoxymethyl, 2-methoxyethyl, 2-ethoxyethyl, 3-methoxypropyl, 4-methoxybutyl, 5-methoxypentyl or 6-methoxyhexyl.

Phenyl-lower alkoxy is, for example, phenyl-$C_1$-$C_4$alkoxy that is unsubstituted or substituted as indicated, such as benzyloxy, 2-phenylethoxy or 3-phenylpropoxy. Accordingly, phenyl-lower alkoxy-lower alkyl is, for example, a phenyl-$C_1$-$C_4$-alkoxy-$C_1$-$C_7$alkyl radical that is unsubstituted or substituted as indicated, such as a benzyloxymethyl, 2-phenylethoxymethyl, 2-benzyloxyethyl, 3-benzyloxypropyl, 4-benzyloxybutyl, 5-benzyloxypentyl or 6-benzyloxyhexyl radical.

Halo-lower alkyl is, for example, halo-$C_1$-$C_7$alkyl, such as halomethyl, 2-haloethyl, 3-halopropyl, 4-halobutyl, 5-halopentyl or 6-halohexyl, in which halogen is chlorine or, especially, fluorine.

Amino-lower alkyl is, for example, amino-$C_1$-$C_7$alkyl, such as aminomethyl, 2-aminoethyl, 3-aminopropyl, 4-aminobutyl, 5-aminopentyl or 6-aminohexyl.

Lower alkylamino is, for example, $C_1$-$C_7$alkylamino, especially $C_1$-$C_4$alkylamino, such as methylamino, ethylamino, propylamino or butylamino, but may also be a $C_5$-$C_6$alkylamino group, such as a pentylamino or hexylamino group. Accordingly, lower alkylamino-lower alkyl is especially $C_1$-$C_4$alkylamino-$C_1$-$C_7$alkyl, such as methylaminomethyl, ethylaminomethyl, propylaminomethyl, butylaminomethyl, 2-methylaminoethyl, 3-methylaminopropyl, 4-methylaminobutyl, 5-methylaminopentyl or 6-methylaminohexyl.

Lower alkanoylamino is, for example, $C_2$-$C_7$-alkanoylamino, especially $C_2$-$C_4$alkanoylamino, such as acetylamino, propionylamino or butyrylamino, but may also be $C_5$-$C_6$-alkanoylamino, such as pivaloylamino. Accordingly, lower alkanoylamino-lower alkyl is especially $C_2$-$C_7$alkanoylamino-$C_1$-$C_7$alkyl, such as acetylaminomethyl, propionylaminomethyl, butyrylaminomethyl, 2-acetylaminoethyl, 3-acetylaminopropyl, 4-acetylaminobutyl, 5-acetylaminopentyl or 6-acetylaminohexyl. By analogy, benzoylamino-lower alkyl shall be understood as being, for example, benzoylamino-$C_1$-$C_7$alkyl that is unsubstituted or substituted in the phenyl moiety, such as benzoylaminomethyl, 2-benzoylaminoethyl, 3-benzoylaminopropyl, 4-benzoylaminobutyl, 5-benzoylaminopentyl or 6-benzoylaminohexyl.

Di-lower alkylamino is, for example, di-$C_1$-$C_7$alkylamino, especially di-$C_1$-$C_4$-alkylamino, such as dimethylamino, diethylamino, N-ethyl-N-methylamino, N-methyl-N-propylamino, dipropylamino or dibutylamino. Accordingly, di-lower alkylamino-lower alkyl is especially di-$C_1$-$C_4$alkylamino-$C_1$-$C_7$alkyl, such as dimethylaminomethyl, diethylaminomethyl, N-ethyl-N-methylaminomethyl, N-methyl-N-propylaminomethyl, dipropylaminomethyl, dibutylaminomethyl, 2-dimethylaminoethyl, 3-dimethylaminopropyl, 4-dimethylaminobutyl, 5-dimethylaminopentyl or 6-dimethylaminohexyl.

N-lower alkanoyl-N-lower alkylamino-lower alkyl is, for example, N-$C_2$-$C_7$-alkanoyl-N-$C_1$-$C_4$alkylamino-$C_1$-$C_7$alkyl, such as N-acetyl-N-methylaminomethyl, N-acetyl-N-ethylaminomethyl, N-propionyl-N-methylaminomethyl, N-butyryl-N-methylaminomethyl, 2-(N-acetyl-N-methylamino)ethyl, 2-(N-propionyl-N-methylamino)ethyl, 2-(N-acetyl-N-ethylamino)ethyl, 3-(N-acetyl-N-methylamino)propyl, 4-(N-acetyl-N-methylamino)butyl, 5-(N-acetyl-N-methylamino)pentyl or 6-(N-acetyl-N-methylamino)hexyl.

4- to 7-membered azacycloalkyl-$C_1$-$C_7$alkyl bonded via an N atom is preferably N,N-lower alkyleneamino-$C_1$-$C_7$alkyl, i.e. azacycloalk-1-yl-$C_1$-$C_7$alkyl, for example pyrrolidinomethyl, piperidinomethyl, morpholinomethyl, 2-pyrrolidinoethyl, 2-piperidinoethyl, 3-pyrrolidinopropyl, 3-piperidinopropyl, 4-pyrrolidinobutyl, 4-piperidinobutyl, 5-pyrrolidinopentyl, 5-piperidinopentyl, 6-pyrrolidinohexyl or 6-piperidinohexyl.

4- to 7-membered azacycloalkyl-$C_1$-$C_7$alkyl bonded via a carbon atom is preferably azacycloalk-3-yl-$C_1$-$C_7$alkyl or -4-yl-$C_1$-$C_7$alkyl, for example piperidin-4-ylmethyl, 2-(piperidin-4-yl)ethyl, 3-(piperidin-4-yl)propyl or 4-(piperidin-4-yl)butyl.

5- to 7-membered N-$C_2$-$C_7$alkanoylazacycloalkyl-$C_1$-$C_7$alkyl bonded via a carbon atom is preferably 1-$C_2$-$C_7$alkanoylazacycloalk-3-yl-$C_1$-$C_7$alkyl or -4-yl-$C_1$-$C_7$alkyl, for example 1-acetylpiperidin-4-ylmethyl, 2-(1-acetylpiperidin-4-yl)ethyl, 3-(1-acetylpiperidin-4-yl)propyl or 4-(1-acetylpiperidin-4-yl)butyl.

5- to 7-membered N-$C_1$-$C_4$alkylazacycloalkyl-$C_1$-$C_7$alkyl bonded via a carbon atom is preferably N-$C_1$-$C_4$alkylazacycloalk-3-yl-$C_1$-$C_7$alkyl or -4-yl-$C_1$-$C_7$alkyl, for example 1-methylpiperidin-4-yl)methyl, 1-ethylpiperidin-4-ylmethyl, 2-(1-methylpiperidin-4-yl)ethyl, 2-(1-ethylpiperidin-4-yl)ethyl, 3-(1-methylpiperidin-4- yl)propyl, 3-(1-ethylpiperidin-4-yl)propyl, 4-(1-methylpiperidin-4-yl)butyl or 4-(1-ethylpiperidin4-yl)butyl.

5- to 7-membered N-benzoylazacycloalkyl-$C_1$-$C_7$alkyl that is bonded via a carbon atom and unsubstituted or substituted in the phenyl moiety is preferably N-$C_1$-$C_4$benzoylazacycloalk-3-yl-$C_1$-$C_7$alkyl, or -4-yl-$C_1$-$C_7$alkyl, for example 1-benzoylpiperidin-4-ylmethyl, 2-(1-benzoylpiperidin-4-yl)ethyl, 3-(1-benzoylpiperidin-4-yl)propyl or 4-(1-benzoylpiperidin-4-yl)butyl.

5- to 7-membered diazacycloalk-1-yl-$C_1$-$C_7$alkyl that is bonded via an N atom and is optionally N'-lower alkylated, N'-lower alkanoylated or N'-substituted by a benzoyl group that is unsubstituted or substituted in the phenyl moiety is, for example. N,N-(aza-lower alkylene)amino-$C_1$-$C_7$alkyl, i.e. diazacycloalk-1-yl-$C_1$-$C_7$alkyl, N'-$C_1$-$C_4$alkyldiazacycloalk-1-yl-$C_1$-$C_7$alkyl or N'-$C_2$-$C_7$alkanoylazacycloalk-1-yl-$C_1$-$C_7$alkyl, for example piperazino- or N'-methyl- or N'-acetyl-piperazino-methyl, 2-(piperazino- or N'-methyl- or N'-acetyl-piperazino)-ethyl, 3-(piperazino- or N'-methyl-or N'-acetyl-piperazino)-propyl or 4-(piperazino- or N'-methyl-or N'-acetylpiperazino)-butyl.

5- to 7-membered N,N-(oxa-lower alkylene)amino-$C_1$-$C_7$alkyl, i.e. azoxacycloalk-1-yl-$C_1$-$C_7$alkyl, is, for example, morpholinomethyl, 2-morpholinoethyl, 3-morpholinopropyl or 4-morpholinobutyl.

5- to 7-membered oxacycloalkyl-$C_1$-$C_7$alkyl bonded via a carbon atom is especially 5- to 7-membered oxacycloalk-3-yl-$C_1$-$C_7$alkyl or oxacycloalk-4-yl-$C_1$-$C_7$alkyl, such as tetrahydropyran-4-ylmethyl, 2-(tetrahydropyran-4-yl)ethyl, 3-(tetrahydropyran-4-yl)propyl or 4-(tetrahydropyran-4-yl)butyl.

5- to 7-membered oxacycloalkyl bonded via a carbon atom is especially corresponding oxacycloalk-3-yl or -4-yl, for example tetrahydropyran-4-yl.

5- to 7-membered azacycloalkyl, N-$C_1$-$C_4$alkylazacycloalkyl or N-$C_2$-$C_7$alkanoylazacycloalkyl bonded via a carbon atom is preferably azacycloalk-3-yl or -4-yl or 1-$C_2$-$C_7$alkanoylazacycloalk-3-yl or -4-yl, for example piperidin-4-yl or 1-acetylpiperidin-4-yl, and also N-$C_1$-$C_4$alkylazacycloalk-3-yl or -4-yl or N-benzoylazacycloalk-3-yl or -4-yl that is unsubstituted or substituted in the phenyl moiety, for example 1-methylpiperidin-4-yl or 1-benzoylpiperidin-4-yl.

Lower alkoxycarbonyl is, for example, $C_1$-$C_7$alkoxycarbonyl, especially $C_1$-$C_4$alkoxycarbonyl, such as methoxycarbonyl, ethoxycarbonyl, propoxycarbonyl, isopropoxycarbonyl or butoxycarbonyl, but may also be a $C_5$-$C_7$alkoxycarbonyl group, such as a pentyloxycarbonyl, hexyloxycarbonyl or heptyloxycarbonyl group.

Phenyl-lower alkoxycarbonyl is, for example, phenyl-$C_1$-$C_4$alkoxycarbonyl, such as benzyloxycarbonyl, 2-phenylethoxycarbonyl, 3-phenylpropoxycarbonyl or 4-phenylbutoxycarbonyl.

On account of their amphoteric nature, the compounds of formula I are in the form of internal salts and can form both acid addition salts and salts with bases.

Acid addition salts of compounds of formula I are, for example, pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexyl sulfamates (cyclamates).

Salts of compounds of formula I with bases are, for example, salts thereof with pharmaceutically acceptable bases, such as non-toxic metal salts derived from groups Ia, Ib, IIa and IIb, for example alkali metal salts, especially sodium or potassium salts, alkaline earth metal salts, especially calcium or magnesium salts, and also ammonium salts with ammonia or organic amines or quaternary ammonium bases, such as unsubstituted or C-hydroxylated aliphatic amines, especially mono-, di- or tri-lower alkylamines, for example methyl-, ethyl- or diethyl-amine, mono-, di- or tri-(hydroxy-lower alkyl)amines, such as ethanol-, diethanol- or triethanol-amine, tris-(hydroxymethyl)methylamine or 2-hydroxy-tert.-butylamine, or N-(hydroxy-lower alkyl)-N,N-di-lower alkylamines or N-(polyhydroxy-lower alkyl)-N-lower alkylamines, such as 2-(dimethylamino)ethanol or D-glucamine, or quaternary aliphatic ammonium hydroxides, for example tetrabutylammonium hydroxide.

For isolation or purification purposes it is also possible to use pharmaceutically unsuitable salts. Only the pharmaceutically acceptable, non-toxic salts are used therapeutically, and these salts are therefore preferred.

The invention relates, for example, to compounds of formula I wherein $R_1$ is an aliphatic hydrocarbon radical that is substituted by optionally aliphatically or araliphatically etherified hydroxy, optionally aliphatically substituted amino or by halogen, and $R_2$ is free dihydroxy-lower alkyl, lower alkanoyloxy-lower alkyl, benzoyloxy-lower alkyl, lower alkoxy-lower alkyl, phenyl-lower alkoxy-lower alkyl, halo-lower alkyl, amino-lower alkyl, lower alkylamino-lower alkyl, lower alkanoylamino-lower alkyl, di-lower alkylamino-lower alkyl, N-lower alkyl-N-lower alkanoylamino-lower alkyl, 5- to 7-membered azacycloalkyl-lower alkyl whose azacycloalkyl moiety is bonded via the N atom or a carbon atom and, in the latter case, may be N-lower alkylated, N-lower alkanoylated or N-substituted by a benzoyl group that is unsubstituted or substituted in the phenyl moiety, 5- to 7-membered diazacycloalkyl-lower alkyl whose diazacycloalkyl moiety is bonded via an N atom and is optionally N'-lower alkylated, N'-lower alkanoylated or N'-substituted by a benzoyl group that is unsubstituted or substituted in the phenyl moiety, 5- to 7-membered azoxacycloalkyl-lower alkyl bonded via the N atom, 5- to 7-membered oxacycloalkyl-lower alkyl bonded via a carbon atom, 5- to 7-membered azacycloalkyl that is bonded via a carbon atom and is optionally N-lower alkylated, N-lower alkanoylated or N-substituted by a benzoyl group that is unsubstituted or substituted in the phenyl moiety, or 5- to 7-membered oxacycloalkyl bonded via a carbon atom, and $R_2$ is carboxy, lower alkoxycarbonyl, 4- up to and including 7-membered cycloalkoxycarbonyl or phenyl-lower alkoxycarbonyl, and phenyl radicals in the mentioned groups $R_1$ and/or $R_2$ being unsubstituted or mono-, di- or tri-substituted by lower alkyl, lower alkoxy, halogen, cyano and/or by trifluoromethyl, and their salts.

The invention relates especially, for example, to compounds of formula I wherein $R_1$ is hydroxy-lower alkyl, lower alkoxy-lower alkyl, phenyl-lower alkoxy-lower alkyl, amino-lower alkyl, lower alkylamino-lower alkyl, di-lower alkylamino-lower alkyl, N,N-lower alkyleneamino- or N,N-(aza- or oxa-lower alkylene)amino-lower alkyl, or halo-lower alkyl, and $R_2$ is carboxy, lower alkoxycarbonyl, 4- up to and including 7-membered cycloalkoxycarbonyl or phenyl-lower alkoxycarbonyl, any phenyl radicals in the mentioned groups $R_1$ and/or $R_2$ being unsubstituted or mono-, dior tri-substituted by lower alkyl, lower alkoxy, halogen, cyano and/or by trifluoromethyl, and their salts.

The invention relates especially to compounds of formula I wherein $R_1$ is hydroxy-$C_1$-$C_7$alkyl, such as hydroxymethyl, 2-hydroxyethyl, 3-hydroxypropyl or 4-hydroxybutyl, dihydroxy-$C_2$-$C_7$alkyl, such as 1,3-dihydroxyprop-2-yl, $C_2$-$C_7$-alkanoyloxy-$C_1$-$C_7$alkyl, such as acetoxymethyl, propionyloxymethyl, butyryloxymethyl, 2-acetyloxyethyl, 3-acetyloxypropyl, 4-acetyloxybutyl, 5-acetyloxypentyl or 6-acetyloxyhexyl, benzoyloxy-$C_1$-$C_7$alkyl that is unsubstituted or mono- or di-substituted in the phenyl moiety by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzoyloxymethyl, 2-benzoyloxyethyl, 3-benzoyloxypropyl, 4-benzoyloxybutyl, 5-benzoyloxypentyl or 6-benzoyloxyhexyl, $C_1$-$C_4$alkoxy-$C_1$-$C_7$alkyl, such as methoxymethyl, ethoxymethyl, 2-methoxyethyl, 3-methoxypropyl or 4-methoxybutyl, a phenyl-$C_1$-$C_4$alkoxy-$C_1$-$C_7$alkyl group that is unsubstituted or mono- or di-substituted in the phenyl moiety by $C_1$-$C_4$alkyl, such as methyl, $C_1$-$C_4$alkoxy, such as methoxy, halogen having an atomic number of up to and including 35, such as flourine or chlorine, cyano and/or by trifluoromethyl, such as benzyloxymethyl, 2-benzyloxyethyl, 3-benzyloxypropyl or 4-benzyloxybutyl, halo-$C_1$-$C_7$alkyl, such as halomethyl, 2-haloethyl, 3-halopropyl, 4-halobutyl, 5-halopentyl or 6-halohexyl, in which halogen is chlorine or, especially, fluorine, amino-$C_1$-$C_7$alkyl, such as aminomethyl, 2-aminoethyl, 3-aminopropyl, 4-aminobutyl, 5-aminopentyl or 6-aminohexyl, $C_1$-$C_4$alkylamino-$C_1$-$C_7$alkyl, such as methylaminomethyl, ethylaminomethyl, propylaminomethyl, butylaminomethyl, 2-methylaminoethyl, 3-methylaminopropyl, 4-methylaminobutyl, 5-methylaminopentyl or 6-methylaminohexyl, $C_2$-$C_7$alkanoylamino-$C_1$-$C_7$alkyl, such as acetylaminomethyl, propionylaminomethyl, butyrylaminomethyl, 2-acetylaminoethyl, 3-acetylaminopropyl, 4-acetylaminobutyl, 5-acetylaminopentyl or 6-acetylaminohexyl, N-$C_2$-$C_1$-$C_4$alkylamino-$C_1$-$C_7$alkyl, such as N-acetyl-N-methylaminomethyl, N-acetyl-N-ethylaminomethyl, N-propionyl-N-methylaminomethyl, N-butyryl-N-methylaminomethyl, 2-(N-acetyl-N-methylamino)ethyl, 2-(N-propionyl-N-methylamino)ethyl, 2-(N-acetyl-N-ethylamino)ethyl, 3-(N-acetyl-N-methylamino)propyl, 4-(N-acetyl-N-methylamino)butyl, 5-(N-acetyl-N-methylamino)pentyl or 6-(N-acetyl-N-methylamino)hexyl, di-$C_1$-$C_7$alkylamino-$C_1$-$C_7$alkyl, such as dimethylaminomethyl, diethylaminomethyl, N-ethyl-N-methylaminomethyl, N-methyl-N-propylaminomethyl, di-propylaminomethyl, dibutylaminomethyl, 2-dimethylaminoethyl, 3-dimethylaminopropyl, 4-dimethylaminobutyl, 5-dimethylaminopentyl or 6-dimethylaminohexyl, azacycloalk-1-yl-$C_1$-$C_7$alkyl, such as pyrrolidinomethyl, piperidinomethyl, 2-pyrrolidinoethyl, 2-piperidinoethyl, 3-pyrrolidinopropyl, 3-piperidinopropyl, 4-pyrrolidinobutyl, 4-piperidinobutyl, 5-pyrrolidinopentyl, 5-piperidinopentyl, 6-pyrrolidinohexyl or 6-piperidinohexyl, azacycloalk-3-yl-$C_1$-$C_7$alkyl or -4-yl-$C_1$-$C_7$alkyl, for example piperidin-4-ylmethyl, 2-(piperidin-4-yl)ethyl, 3-(piperidin-4-yl)propyl or 4-(piperidin-4-yl)butyl, 1-$C_2$-$C_7$alkanoylazacycloalk-3-yl-$C_1$-$C_7$alkyl or -4-yl-$C_1$-$C_7$alkyl, for example 1-acetylpiperidin-4-ylmethyl, 2-(1-acetylpiperidin-4-yl)ethyl, 3-(1-acetylpiperidin-4-yl)propyl or 4-(1-acetylpiperidin-4-yl)butyl, N-$C_1$-$C_4$alkylazacycloalk-3-yl-$C_1$-$C_7$alkyl or -4-yl-$C_1$-$C_7$alkyl, for example 1-methylpiperidin-4-ylmethyl, 1-ethylpiperidin-4-ylmethyl, 2-(1-methylpiperidin-4-yl)ethyl, 2-(1-ethylpiperidin-4-yl)ethyl, 3-(1-methylpiperidin-4-yl)propyl, 3-(1-ethylpiperidin-4-yl)propyl, 4-(1-methylpiperidin-4-yl)butyl or 4-(1-ethylpiperidin-4-yl)butyl, N-$C_1$-$C_4$benzoylazacycloalk-3-yl-$C_1$-$C_7$alkyl or -4-yl-$C_1$-$C_7$alkyl, for example 1-benzoylpiperidin-4-ylmethyl, 2-(1-benzoylpiperidin-4-yl)ethyl, 3-(1-benzoylpiperidin-4-yl)propyl or 4-(1-benzoylpiperidin-4-yl)butyl, diazacycloalk-1-yl-$C_1$-$C_7$alkyl, N'-$C_1$-$C_4$alkyldiazacycloalk-1-yl-$C_1$-$C_7$alkyl or N'-$C_2$-$C_7$alkanoylazacycloalk-1-yl-$C_1$-$C_7$alkyl, for example piperazino- or N'-methyl- or N'-acetyl-piperazino-methyl, 2-(piperazino- or N'-methyl- or N'-acetyl-piperazino)-ethyl, 3-(piperazino- or N'-methyl- or N'-acetyl-piperazino)-propyl or 4-(piperazino- or N'-methyl- or N'-acetyl-piperazino)-butyl, azoxacycloalk-1-yl-$C_1$-$C_7$alkyl, for example morpholinomethyl, 2-morpholinoethyl, 3-morpholinopropyl or 4-morpholinobutyl, 5- to 7-membered oxacycloalk-3-yl-$C_1$-$C_7$alkyl or -4-yl-$C_1$-$C_7$alkyl, such as tetrahydropyran-4-ylmethyl, 2-(tetrahydropyran-4-yl)ethyl, 3-(tetrahydropyran-4-yl)propyl or 4-(tetrahydropyran-4-yl)butyl, 5- to 7-membered azacycloalk-3-yl or -4-yl or 1-$C_2$-$C_7$-alkanoylazacycloalk-3-yl or -4-yl, for example piperidin-4-yl or 1-acetylpiperidin-4-yl, N-$C_1$-$C_4$alkylazacycloalk-3-yl or -4-yl or N-benzoylazacycloalk-3-yl or -4-yl that is unsubstituted or substituted in the phenyl moiety, for example 1-methylpiperidin-4-yl or 1-benzoylpiperidin-4-yl, or 5- to 7-membered oxacycloalk-3-yl or -4-yl, for example tetrahydropyran-4-yl, and $R_2$ is carboxy, $C_1$-$C_4$alkoxycarbonyl, such as methoxycarbonyl or ethoxycarbonyl, 5- to 7-membered cycloalkoxycarbonyl, such as cyclopentyloxy- or cyclohexyloxy-carbonyl, or phenyl-$C_1$-$C_4$alkoxycarbonyl that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzyloxycarbonyl or 2-phenylethoxycarbonyl, and their salts, especially their pharmaceutically acceptable salts.

The invention relates especially, for example, to compounds of formula I wherein $R_1$ is hydroxy-$C_1$-$C_7$alkyl, such as hydroxymethyl, 2-hydroxyethyl, 3-hydroxypropyl or 4-hydroxybutyl, $C_1$-$C_4$alkoxy-$C_1$-$C_7$alkyl, such as methoxymethyl, ethoxymethyl, 2-methoxyethyl, 2-ethoxyethyl, 3-methoxypropyl or 4-methoxybutyl, a phenyl-$C_1$-$C_4$alkoxy-$C_1$-$C_7$alkyl group that is unsubstituted or mono-, di- or tri-substituted in the phenyl moiety by $C_1$-$C_4$alkoxy, such as methoxy, halogen having an atomic number of up to and including 35, such as fluorine or chlorine, cyano and/or by trifluoromethyl, such as a benzyloxymethyl, 2-benzyloxyethyl, 3-benzyloxypropyl or 4-benzyloxybutyl group, amino-$C_1$-$C_7$alkyl, such as aminomethyl, 2-aminoethyl, 3-aminopropyl, 4-aminobutyl, 5-aminopentyl or 6-aminohexyl, $C_1$-$C_4$alkylamino-$C_1$-$C_7$alkyl, such as methylaminomethyl, ethylaminomethyl, propylaminomethyl, butylaminomethyl, 2-methylaminoethyl, 3-methylaminopropyl, 4-methylaminobutyl, 5-methylaminopentyl or 6-methylaminohexyl, $C_2$-$C_7$alkanoylamino-$C_1$-$C_7$alkyl, such as acetylaminomethyl, propionylaminomethyl, butyrylaminomethyl, 2-acetylaminoethyl, 3-acetylaminopropyl, 4-acetylaminobutyl, 5-acetylaminopentyl or 6-acetylaminohexyl, di-$C_1$-$C_7$alkylamino-$C_1$-$C_7$alkyl, such as dimethylaminomethyl, diethylaminomethyl, N-ethyl-N-methylaminomethyl, N-methyl-N-propylaminomethyl, dipropylaminomethyl, dibutylaminomethyl, 2-dimethylaminoethyl, 3-dimethylaminopropyl, 4-dimethylaminobutyl, 5-dimethylaminopentyl or 6-dimethylaminohexyl, 5- to 7-membered N,N-(aza- or oxa-alkylene)amino-$C_1$-$C_7$alkyl, such as pyrrolidinomethyl, piperidinomethyl, morpholinomethyl, piperazino- or N'-methyl- or N'-acetylpiperazino-methyl, 2-pyrrolidinoethyl, 2-piperidinoethyl, 2-morpholinoethyl, 3-pyrrolidinopropyl, 3-piperidinopropyl, 3-morpholinopropyl, 4-pyrrolidinobutyl, 4-piperidinobutyl, 5-pyrrolidinopentyl, 5-piperidinopentyl or 6-piperidinohexyl, or halo-$C_1$-$C_7$alkyl, such as halomethyl, 2-haloethyl, 3-halopropyl, 4-halobutyl, 5-halopentyl or 6-halohexyl, in which halogen is chlorine or, especially, fluorine, and $R_2$ is carboxy, $C_1$-$C_4$alkoxycarbonyl, such as methoxycarbonyl or ethoxycarbonyl, 5- to 7-membered cycloalkoxycarbonyl, such as cyclopentyloxy- or cyclohexyloxy-carbonyl, or phenyl-$C_1$-$C_4$alkoxycarbonyl that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzyloxycarbonyl or 2-phenylethoxycarbonyl, and their salts, especially their pharmaceutically acceptable salts.

The invention relates preferably to compounds of formula I wherein $R_1$ is hydroxy-$C_1$-$C_7$alkyl, such as hydroxymethyl, 2-hydroxyethyl or 3-hydroxypropyl, benzoyloxy-$C_1$-$C_7$alkyl that is unsubstituted or mono- or di-substituted in the phenyl moiety by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as 2-benzoyloxyethyl, $C_1$-$C_4$alkoxy-$C_1$-$C_7$alkyl, such as ethoxymethyl or 2-methoxyethyl, phenyl-$C_1$-$C_4$alkoxy-$C_1$-$C_7$alkyl that is unsubstituted or mono- or di-substituted in the phenyl moiety by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzyloxymethyl or 2-benzyloxyethyl, halo-$C_1$-$C_7$alkyl, such as halomethyl, in which halogen is chlorine or, especially, fluorine, amino-$C_4$-$C_7$alkyl, such as 4-aminobutyl or 6-aminohexyl, N-$C_2$-$C_4$alkylamino-$C_1$-$C_7$alkyl, such as N-acetyl-N-methylaminomethyl, 5- to 7-membered azacycloalk-3-yl or -4-yl or 1-$C_2$-$C_7$-alkanoylazacycloalk-3-yl or -4-yl, for example piperidin-4-yl or 1-acetylpiperidin-4-yl, and $R_2$ is carboxy, $C_1$-$C_4$alkoxycarbonyl, such as methoxycarbonyl or ethoxycarbonyl, or phenyl-$C_1$-$C_4$alkoxycarbonyl that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzyloxycarbonyl or 2-phenylethoxycarbonyl, and their salts, especially their pharmaceutically acceptable salts.

The invention relates especially, on the one hand, to compounds of formula I wherein $R_1$ is hydroxy-$C_1$-$C_4$alkyl, such as hydroxymethyl, 2-hydroxyethyl, 3-hydroxypropyl or 4-hydroxybutyl, $C_1$-$C_4$alkoxy-$C_1$-$C_4$alkyl, such as methoxymethyl, ethoxymethyl, 2-methoxyethyl, 3-methoxypropyl or 4-methoxybutyl, a phenyl-$C_1$-$C_4$alkoxy-$C_1$-$C_4$alkyl group that is unsubstituted or mono-, di- or tri-substituted in the phenyl moiety by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as a benzyloxymethyl, 2-benzyloxyethyl, 3-benzyloxypropyl or 4-benzyloxybutyl group, or halo-$C_1$-$C_4$alkyl, such as halomethyl, 2-haloethyl, 3-halopropyl, 4-halobutyl, 5-halopentyl or 6-halohexyl, in which halogen is chlorine or, especially, fluorine, and $R_2$ is carboxy, $C_1$-$C_4$alkoxycarbonyl, such as methoxycarbonyl or ethoxycarbonyl, 5- to 7-membered cycloalkoxycarbonyl, such as cyclopentyloxy- or cyclohexyloxy-carbonyl, or phenyl-$C_1$-$C_4$alkoxycarbonyl that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as benzyloxycarbonyl or 2-phenylethoxycarbonyl, and their salts, especially their pharmaceutically acceptable salts.

The invention relates especially, on the other hand, to compounds of formula I wherein $R_1$ is amino-$C_1$-$C_7$alkyl, such as aminomethyl, 2-aminoethyl, 3-aminopropyl, 4-aminobutyl, 5-aminopentyl, 6-aminohexyl or 7-aminoheptyl, $C_1$-$C_4$alkylamino-$C_1$-$C_7$alkyl, such as methylaminomethyl, ethylaminomethyl, propylaminomethyl, butylaminomethyl, 2-methylaminoethyl, 3-methylaminopropyl, 4-methylaminobutyl, 5-methylaminopentyl or 6-methylaminohexyl, $C_2$-$C_7$alkanoylamino-$C_1$-$C_7$alkyl, such as acetylaminomethyl, propionylaminomethyl, butyrylaminomethyl, 2-acetylaminoethyl, 3-acetylaminopropyl, 4-acetylaminobutyl, 5-acetylaminopentyl or 6-acetylaminohexyl, di-$C_1$-$C_4$alkylamino-$C_1$-$C_7$alkyl, such as dimethylaminomethyl, diethylaminomethyl, N-ethyl-N-methylaminomethyl, N-methyl-N-propylaminomethyl, dipropylaminomethyl, dibutylaminomethyl, 2-dimethylaminoethyl, 3-dimethylaminopropyl, 4-dimethylaminobutyl, 5-dimethylaminopentyl or 6-dimethylaminohexyl, 5- to 7-membered N,N-(aza- or oxa-alkylene)amino-$C_1$-$C_7$alkyl, such as pyrrolidinomethyl, piperidinomethyl, morpholinomethyl, piperazino- or N'-methyl- or N'-acetylpiperazino-methyl, pyrrolidinoethyl, piperidinoethyl, morpholinoethyl, pyrrolidinopropyl, piperidinopropyl, morpholinopropyl, pyrrolidinobutyl, piperidinobutyl, pyrrolidinopentyl, piperidinopentyl or piperidinohexyl, and $R_2$ is carboxy, $C_1$-$C_4$alkoxycarbonyl, such as methoxycarbonyl or ethoxycarbonyl, 5- to 7-membered cycloalkoxycarbonyl, such as cyclopentyloxy- or cyclohexyloxy-carbonyl, or phenyl-$C_1$-$C_4$alkoxycarbonyl that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifuoromethyl, such as benzyloxycarbonyl or 2-phenylethoxycarbonyl, and their salts, especially their pharmaceutically acceptable salts.

The invention relates more especially to compounds of formula I wherein $R_1$ is hydroxy-$C_1$-$C_7$alkyl, such as hydroxymethyl, $C_1$-$C_4$alkoxy-$C_1$-$C_7$alkyl, such as methoxymethyl, ethoxymethyl or 2-methoxyethyl, benzoyloxy-$C_1$-$C_4$alkyl, such as 2-benzoyloxyethyl, phenyl-$C_1$-$C_4$alkoxy-$C_1$-$C_7$alkyl, such as benzyloxymethyl or 2-benzyloxyethyl, amino-$C_4$-$C_7$alkyl, such as 4-aminobutyl or 6-aminohexyl, N-$C_2$-$C_7$alkanoyl-N-$C_1$-$C_4$alkylamino-$C_2$-$C_7$alkyl, such as 2-(N-acetyl-N-methylamino)ethyl, 5-to 7-membered azacycloalk-3-yl or -4-yl or 1-$C_2$-$C_7$alkanoylazacycloalk-3-yl or -4-yl, such as piperidin-4-yl or 1-acetylpiperidin-4-yl, or halo-$C_1$-$C_4$alkyl, in which halogen is chlorine or, especially, fluorine, such as 2-haloethyl, and $R_2$ is carboxy or $C_1$-$C_4$alkoxycarbonyl, such as methoxycarbonyl or ethoxycarbonyl, and their salts, especially their pharmaceutically acceptable salts.

The invention relates preferably, on the one hand, to compounds of formula I wherein $R_1$ is amino-$C_4$-$C_7$alkyl, such as 4-aminobutyl or 6-aminohexyl, N-$C_1$-$C_4$alkanoyl-N-$C_1$-$C_4$alkylamino-$C_1$-$C_7$alkyl, piperdin-4-yl or 1-$C_2$-$C_7$alkanoylpiperidin-4-yl, such as 1-acetylpiperidin-4-yl, and $R_2$ is carboxy or $C_1$-$C_4$alkoxycarbonyl, such as methoxycarbonyl or ethoxycarbonyl, and their salts.

The invention relates preferably, on the other hand, to compounds of formula I wherein $R_1$ is $C_1$-$C_4$alkoxy-$C_1$-$C_4$alkyl, such as methoxymethyl, ethoxymethyl or 2-methoxyethyl, phenyl-$C_1$-$C_4$alkoxy-$C_1$-$C_4$alkyl, such as benzyloxymethyl or 2-benzyloxyethyl, benzoyloxy-$C_1$-$C_4$alkyl, such as 2-benzoyloxyethyl, hydroxy-$C_1$-$C_4$alkyl, such as hydroxymethyl or 2-hydroxyethyl, or halo-$C_2$-$C_4$alkyl, such as 2-fluoroethyl, and $R_2$ is carboxy or $C_1$-$C_4$alkoxycarbonyl, such as methoxycarbonyl or ethoxycarbonyl, and their salts.

The invention relates very especially, on the one hand, to compounds of formula I wherein $R_1$ is amino-$C_4$-$C_7$alkyl, such as 4-aminobutyl, 5-aminopentyl, 6-aminohexyl or 7-aminoheptyl, and $R_2$ is carboxy, $C_1$-$C_4$alkoxycarbonyl, such as methoxycarbonyl or ethoxycarbonyl, or a phenyl-$C_1$-$C_4$alkoxycarbonyl group that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as a benzyloxycarbonyl or 2-phenylethoxycarbonyl group, and their salts, especially their pharmaceutically acceptable salts.

The invention relates very especially, on the other hand, to compounds of formula I wherein $R_1$ is $C_1$-$C_4$alkoxy-$C_2$-$C_4$alkyl, such as 2-methoxyethyl, 2-ethoxyethyl, 3-methoxypropyl or 4-methoxybutyl, hydroxy-$C_2$-$C_4$alkyl, such as 2-hydroxyethyl, 3-hydroxypropyl or 4-hydroxybutyl, or halo-$C_2$-$C_4$alkyl, such as 2-fluoroethyl, 2-chloroethyl, 3-fluoropropyl or 4-fluorobutyl, and $R_2$ is carboxy, $C_1$-$C_4$alkoxycarbonyl, such as methoxycarbonyl or ethoxycarbonyl, or a phenyl-$C_1$-$C_4$alkoxycarbonyl group that is unsubstituted or mono- or di-substituted by $C_1$-$C_4$alkyl, such as methyl, $C_1$-$C_4$alkoxy, such as methoxy, halogen having an atomic number of up to and including 35, such as fluorine or chlorine, cyano and/or by trifluoromethyl, such as a benzyloxycarbonyl or 2-phenylethoxycarbonyl group, and their salts, especially their pharmaceutically acceptable salts.

The invention relates specifically to the compounds of formula I mentioned in the Examples and their salts, especially their pharmaceutically acceptable salts.

The process for the preparation of the compounds according to the invention is as follows:
in a compound of formula II

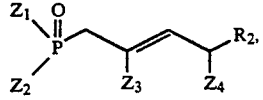

(II)

wherein $Z_1$, $Z_2$ are optionally protected hydroxy, $Z_3$ is an aliphatic hydrocarbon radical that is substituted by optionally protected or acylated or aliphatically or araliphatically etherified hydroxy, by halogen, by optionally protected or acylated and/or aliphatically substituted amino or by an aza-, diaza-, azoxa- or oxacycloaliphatic radical, or is an oxacycloaliphatic hydrocarbon radical bonded via a carbon atom, or is an optionally protected or aliphatically N-substituted or N-acylated azacycloaliphatic hydrocarbon radical, and $Z_4$ is protected amino, protected amino $Z_4$ and, if present, protected amino as a constituent of $Z_3$ is converted into amino and, if present, protected hydroxy $Z_1$, $Z_2$ and/or protected hydroxy as a constituent of $Z_3$ is converted into hydroxy and, if present, a protected azacycloaliphatic hydrocarbon radical $Z_3$ is freed and, if desired, a resulting compound is converted into a different compound of formula I, an isomeric mixture obtainable in accordance with the process is separated into its components and the preferred isomer is separated, and/or a free compound obtainable in accordance with the process is converted into a salt or a salt obtainable in accordance with the process is converted into the corresponding free compound.

In starting materials of formula II, protected hydroxy $Z_1$ and/or $Z_2$ is, for example, etherified, especially aliphatically or aromatically etherified, hydroxy, protected hydroxy $Z_3$ is, for example, acylated or silylated hydroxy, and protected amino $Z_4$ and, if present, protected amino as a constituent of $Z_3$ is, for example, acylated amino.

Aliphatically etherified hydroxy is, for example, lower alkoxy, such as methoxy, ethoxy or, especially, isopropoxy. Aromatically etherified hydroxy is, for example, phenoxy that is unsubstituted or substituted by lower alkyl, lower alkoxy, halogen, cyano and/or by nitro.

Acylated hydroxy contains as the acyl group, for example, the acyl radical of an araliphatic carboxylic acid or of a semi-ester of carbonic acid and is, for example, lower alkanoyloxy or a phenyl-lower alkanoyloxy or phenyl-lower alkoxycarbonyloxy group that is unsubstituted or substituted in the phenyl moiety by lower alkyl, lower alkoxy, halogen, cyano and/or by trifluoromethyl, for example benzyloxycarbonyloxy.

Silylated hydroxy is, for example, tri-lower alkylsilyloxy, for example trimethyl- or tributyl-silyloxy.

Acylated amino contains as the acyl group, for example, acyl derived from a suitable organic acid, such as formic acid, or from an araliphatic or aromatic semi-ester of carbonic acid. Accordingly, acylated amino is, for example, formylamino, lower alkoxycarbonylamino, such as methoxy-, ethoxy- or tert.-butoxycarbonylamino, or a phenyl-lower alkoxycarbonylamino or or phenoxycarbonylamino group that is unsubstituted or substituted in the phenyl moiety by lower alkyl, lower alkoxy, halogen, cyano and/or by nitro, such as benzyloxycarbonylamino, substituted by lower alkyl, lower alkoxy, halogen, cyano and/or by nitro.

The freeing of the protected groups from compounds of formula II, i.e. of hydroxy from protected hydroxy groups $Z_1$, $Z_2$ and/or from protected hydroxy groups as a constituent of $Z_3$, or of amino from protected amino groups $Z_4$ and, if present, from protected amino groups as a constituent of $Z_3$, is carried out, for example, by treatment with an acidic agent, for example with a tri-lower alkylhalosilane, such as trimethylbromosilane, tributylbromosilane or trimethyliodosilane. The operation is preferably carried out in an inert solvent, such as a halogenated aliphatic hydrocarbon, for example dichloromethane or, secondly, tri- or tetra-chloromethane, trichloroethane or tetrachloroethane, for example in a temperature range of from approximately −25° to approximately +50° C., preferably of approximately from 0° to 30° C., for example at room temperature, i.e. at approximately from 15° to 25° C., advantageously under substantially anhydrous conditions and under an inert gas, such as argon or nitrogen. Working up is preferably carried out with the addition of a hydrogen halide acceptor, especially an aliphatic epoxy compound, such as an epoxy-lower alkane, for example propylene oxide in a lower alkanol, such as ethanol.

In a preferred form, for example compounds of formula II wherein $Z_1$ and $Z_2$ are lower alkoxy, for example isopropoxy, and $Z_4$ is lower alkanoylamino, such as formylamino, are used as starting materials and are treated in an aliphatic halogenated hydrocarbon, such as dichloromethane, at from approximately 15° to approximately 25° C., with a tri-lower alkylbromosilane, such as trimethylbromosilane or tributylbromosilane; the mixture is left for a time, for example from 2 to 30 hours, to complete the reaction, and then an ethanolic solution of propylene oxide is added and the product is removed by filtration.

Starting materials of formula II are prepared, for example, by reacting an α,β-unsaturated aldehyde of formula IIa

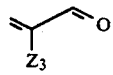  (IIa)

with an α-isocyanoacetic acid ester of formula IIb

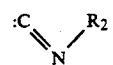  (IIb)

in a manner known per se, for example in the presence of a copper or gold catalyst, for example copper(I) oxide or bis(cyclohexylisocyanide)gold(I) tetrafluoroborate, to give the corresponding 5-substituted 2-oxazoline-4-carboxylic acid ester of formula IIc

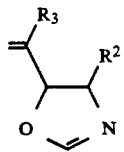  (IIc)

converting the ester of formula IIc by hydrolysis, for example in aqueous tetrahydrofuran, into the corresponding open-chained ester of formula IId

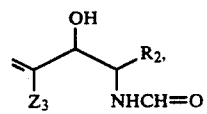  (IId)

converting the ester of formula IId by treatment with thionyl bromide in a manner known per se into the corresponding ω-bromic ester of formula IIe

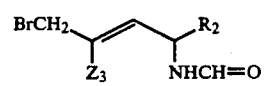  (IIe)

and reacting the ester of formula IIe further in a manner known per se with a phosphorous acid triester of the formula $P(Z_a)(Z_b)(Z_c)$, wherein $Z_a$, $Z_b$ and $Z_c$ are identical or different hydroxy groups protected in an ether form, such as a tri-lower alkyl phosphite, for example triisopropyl phosphite, to give the corresponding compound of formula II'

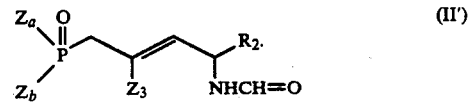  (II')

Compounds obtainable in accordance with the process can be converted in customary manner into different compounds of formula I.

For example, free and esterified carboxy groups $R_2$ can be converted in customary manner into one another. In particular, esterified carboxy $R_2$ can be converted into carboxy by hydrolysis, or free carboxy $R_2$ can be converted into esterified carboxy by reaction with an alcohol. Furthermore, esterified carboxy $R_2$ can be transesterified to form a different esterified carboxy group. These transesterification reactions are carried out in customary manner under hydrolytic, alcoholytic or transesterifying conditions.

The hydrolysis of carboxylic acid esters (I; $R_2$=esterified carboxy) is carried out in customary manner, if necessary in the presence of an acidic or basic agent, such as a mineral acid, for example hydrochloric acid or sulfuric acid, or a base, such as an alkali metal hydroxide, for example sodium hydroxide.

The transesterification of esters (I; $R_2$=esterified carboxy) with alcohols is usually carried out under conditions of acid-catalysis or base-catalysis, for example in the presence of a catalytic amount of a mineral acid, such as hydrochloric acid or sulfuric acid, or of a metal base, such as sodium hydroxide, or by employing the alcohol component in the form of a metal alcoholate, for example an alkali metal alcoholate.

Furthermore, in aliphatic hydrocarbon radicals substituted by araliphatically etherified hydroxy, such as α-phenyl-lower alkoxy-lower alkyl radicals $R_1$, the α-phenyl-lower alkoxy group can be converted into hydroxy by reduction, for example by treatment with hydrogen in the presence of a hydrogenation catalyst, such as palladium-on-carbon or Raney nickel.

Resulting salts can be converted into the free compounds in a manner known per se, for example by treatment with a base, such as an alkali metal hydroxide, a metal carbonate, a metal hydrogen carbonate or ammonia, or with another salt-forming base mentioned at the beginning, or with an acid, such as a mineral acid, for example hydrochloric acid, or another salt-forming acid mentioned at the beginning.

Resulting salts can be converted into different salts in a manner known per se, in the case of acid addition salts, for example, by treatment with a suitable metal salt, such as a sodium, barium or silver salt, of a different acid in a suitable solvent in which an inorganic salt being formed is insoluble and therefore is eliminated from the reaction equilibrium, and in the case of base salts, by freeing the free acid and converting it into a salt again.

The compounds of formula I, including their salts, may also be obtained in the form of hydrates or include the solvent used for crystallisation.

In view of the close relationship between the novel compounds in free form and in the form of their salts, hereinbefore and hereinafter any reference to the free compounds or their salts should be understood as including also the corresponding salts or free compounds, respectively, where appropriate and expedient.

Resulting diastereoisomeric mixtures and mixtures of racemates can be separated into the pure diastereoisomers and racemates in known manner on the basis of the physicochemical differences between the constituents, for example by chromatography and/or fractional crystallisation.

Furthermore, resulting racemates can be separated into the optical antipodes by known methods, for example by recrystallisation from an optically active solvent, with the aid of microorganisms, or by reaction of the resulting diastereoisomeric mixture or racemate with an optically active auxiliary compound, for example, according to the acid, basic or functionally modifiable groups contained in compounds of formula I, with an optically active acid, base or an optically active alcohol, to form mixtures of diastereoisomeric salts or functional derivatives, such as esters, and separation thereof into the diastereoisomers from which the desired enantiomer can be freed in the customary manner. Suitable bases, acids and alcohols are, for example, amino acids, especially lysine, optically active alkaloid bases, such as strychnine, cinchonine or brucine, or D- or L-(1-phenyl)ethylamine, 3-pipecoline, ephedrine, amphetamine and similar synthetically obtainable bases, optically active carboxylic or sulfonic acids, such as quinic acid or D- or L-tartaric acid, D- or L-di-o-toluyltartaric acid, D- or L-malic acid, D- or L-mandelic acid or D- or L-camphorsulfonic acid, and optically active alcohols, such as borneol or D- or L-(1-phenyl)ethanol.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials developed specifically for the preparation of the compounds according to the invention, especially to those starting materials resulting in the compounds of formula I that were described at the beginning as being preferred, to processes for the preparation thereof and to their use as intermediates.

The novel compounds of formula I can be used, for example, in the form of pharmaceutical preparations that contain a therapeutically effective amount of the active ingredient for anticonvulsive medicaments for the treatment of conditions sensitive to NMDA-antagonism, specifically epilepsy, ischaemia and/or migraine, optionally together with inorganic or organic, solid or liquid, pharmaceutically acceptable carriers, which are suitable for enteral, e.g. oral, or parenteral administration. There are used, for example, tablets or gelatin capsules that contain the active ingredient together with diluents, for example lactose, dextrose, saccharose, mannitol, sorbitol, cellulose, and/or lubricants, for example silica, talc, stearic acid or salts thereof, such as magnesium or calcium stearate, and/or polyethylene glycol. Tablets can also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colouring agents, flavourings and sweeteners. The novel compounds of formula I can also be used in the form of parenterally administrable preparations or in the form of infusion solutions. Such solutions are preferably isotonic aqueous solutions or suspensions which, for example in the case of lyophilised preparations that contain the active ingredient on its own or together with a carrier, for example mannitol, can be prepared before use. The pharmaceutical preparations may be sterilised and/or may contain adjuncts, for example preservatives, stabilisers, wetting agents and/or emulsifiers, solubilisers, salts for regulating the osmotic pressure and/or buffers. The pharmaceutical preparations in question, which, if desired, may contain further pharmacologically active substances, are prepared in a manner known per se, for example by means of conventional mixing, granulating, confectioning, dissolving or lyophilising processes, and contain approximately from 0.1% to 100%, especially from approximately 1% to approximately 50%, in the case of lyophilisates up to approximately 100%, active ingredient.

The invention relates also to the use of the compounds of formula I, preferably in the form of pharmaceutical preparations, as anticonvulsive medicaments for treatment of conditions sensitive to NMDA-antagonism, specifically epilepsy, ischaemia and/or migraine. The dosage may depend on various factors, such as the mode of administration and the species, age and/or individual condition. The daily doses are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples illustrate the invention; temperatures are given in degrees Celsius and pressures in mbar.

EXAMPLE 1

3.57 g (8.5 mmol) of 6-acetoxy-4-diisopropylphosphonomethyl-2-formylamino-hex-3-enoic acid ethyl ester are dissolved in 22 ml of dichloromethane, and 4.4 ml (34 mmol) of trimethylbromosilane are added dropwise at room temperature. The mixture is left to stand at room temperature for 22 hours, 22 ml of ethanol are added dropwise, the mixture is left to stand for a further 22 hours and is concentrated by evaporation in a rotary evaporator, the residue is dissolved in 22 ml of ethanol, and a mixture of 22 ml of propylene oxide and 22 ml of ethanol is added dropwise. A suspension forms, which is stirred for a further 90 minutes and then filtered with suction. 2-amino-6-hydroxy-4-phosphonomethyl-hex-3-enoic acid ethyl ester having a melting point of 195° (decomp.) is obtained.

The starting material can be prepared, for example, as follows:

13.0 g (100 mmol) of acetic acid (4-oxo)butyl ester, 92.0 g (112.6 mmol) of dimethylammonium chloride and 10.8 ml (117 mmol) of 37% formaldehyde solution are heated at 100° for one hour with stirring. The mixture is allowed to cool and is extracted 3 times with 30 ml of diethyl ether each time. The organic phases are combined, washed with saturated sodium chloride solution, dried over magnesium sulfate and concentrated to dryness by evaporation. Acetic acid (3-formyl)but-3-enyl ester is obtained in the form of a colourless oil which can be reacted further without further purification.

13.5 g (95 mmol) of acetic acid (3-formyl)but-3-enyl ester and 10.4 g (95 mmol) of isocyanoacetic acid ethyl ester are added dropwise to a suspension of 0.38 g of copper(I) oxide in 50 ml of benzene. When the exothermic reaction has subsided, the mixture is stirred at room temperature for a further 45 minutes, filtered over Hyflo ® and concentrated to dryness by evaporation. The residue is taken up in 75 ml of tetrahydrofuran, 25 ml of water are added, and the mixture is heated under reflux for 4 hours with stirring. The mixture is concentrated to dryness by evaporation and chromatographed on silica gel with toluene/isopropanol (9:1) as eluant.

6-acetoxy-2-formylamino-3-hydroxy-4-methylene-hexanoic acid ethyl ester is obtained in the form of a brownish oil.

9.19 g (35.9 mmol) of 6-acetoxy-2-formylamino-3-hydroxy-4-methylene-hexanoic acid ethyl ester are dissolved in 100 ml of dichloromethane, and 3.34 ml (43.1 mmol) of thionyl bromide are added dropwise at room temperature. After one hour, 10 ml of water are added and the mixture is stirred vigorously for 10 minutes. The organic phase is separated off, washed in succession with water, saturated potassium hydrogen carbonate solution and again with water, dried over magnesium sulfate, filtered and concentrated by evaporation. 6-acetoxy-4-bromomethyl-2-formylamino-hex-3-enoic acid ethyl ester is obtained in the form of a brownish oil.

8.7 g (25 mmol) of 6-acetoxy-4-bromomethyl-2-formylamino-hex-3-enoic acid ethyl ester and 21 ml (75 mmol) of triisopropyl phosphite (90%) are heated to from 80° to 90° C. and stirred for 19 hours under a pressure of approximately 100 mbar. The excess triisopropyl phosphite is distilled off and the evaporation residue is chromatographed on 150 g of silica gel with first ethyl acetate and then ethyl acetate/ethanol (9:1) as eluants. 6-acetoxy-4-diisopropylphosphonomethyl-2-formylamino-hex-3-enoic acid ethyl ester is obtained in the form of a yellowish oil.

EXAMPLE 2

0.415 g (1.55 mmol) of 2-amino-6-hydroxy-4-phosphonomethyl-hex-3-enoic acid ethyl ester is heated under reflux in 3 ml of water for 24 hours. The reaction mixture is concentrated by evaporation, purified by chromatography on 10 g of silica gel with ethanol/water (1:1) as eluant, and crystallised from ethanol. 2-amino-6-hydroxy-4-phosphonomethyl-hex-3-enoic acid having a melting point >300° is obtained.

EXAMPLE 3

0.5 g (1.0 mmol) of 8-(N-benzyloxycarbonylamino)-4-diethylphosphonomethyl-2-formylamino-oct-3-enoic acid methyl ester is heated under reflux in 5.0 ml of 6N hydrochloric acid for 6 hours. Concentration to dryness by evaporation yields 2,8-diamino-4-phosphonomethyl-oct-3-enoic acid dihydrochloride in the form of a rubber-like solid which is recrystallised from acetonitrile; m.p. 128° (decomp.).

The starting material can be prepared as follows:

7.06 ml (47 mmol) of chloroformic acid benzyl ester are added dropwise to a solution of 5.52 g (47 mmol) of 6-aminohexan-1-ol and 3.95 g (47 mmol) of sodium hydrogen carbonate in 100 ml of acetone and 50 ml of water. The mixture is stirred at room temperature for 18 hours and concentrated to approximately 70 ml, and the white precipitate is filtered off, washed with approximately 20 ml of water, taken up in 250 ml of methylene chloride and dried over magnesium sulfate; the magnesium sulfate is filtered off and the residue is concentrated to dryness by evaporation. 6-(N-benzyloxycarbonylamino)hexan-1-ol is obtained in the form of white crystals having a melting point of 58°-60°.

0.32 ml (4.40 mmol) of dimethyl sulfoxide is added dropwise under nitrogen to a solution of 0.19 ml (2.20 mmol) of oxalyl chloride in 10 ml of methylene chloride which is being stirred at −50°. The mixture is stirred for 15 minutes, and then 0.5 g (2 mmol) of 6-(N-benzyloxycarbonylamino)hexan-1-ol is added. Stirring is continued at −50° for 25 minutes, 1.78 ml (10 mmol) of N-ethyl-N,N-diisopropylamine are added dropwise and the mixture is poured into 10 ml of ice-water. The organic phase is separated off and the aqueous phase is extracted with 10 ml of methylene chloride. The organic phases are combined, washed twice with 5 ml of N-hydrochloric acid each time and once with 10 ml of saturated sodium chloride solution, dried over magnesium sulfate and concentrated to dryness by evaporation. The resulting oil is purified by chromatography on silica gel with hexane/ethyl acetate (1:1) as eluant. 6-(N-benzyloxycarbonylamino)hexanal is obtained.

2.44 g (30 mmol) of 37% aqueous formaldehyde solution are added to a solution of 1.5 g (17 mmol) of anhydrous piperazine and 2.03 g (34 mmol) of acetic acid in 18.7 ml of water. The mixture is stirred at 25° for 15 minutes, and then 7.48 g (30 mmol) of 6-(N-benzyloxycarbonylamino)hexanal are added thereto. The reaction mixture is heated under reflux for 2 hours and then cooled with ice-water and extracted twice with 50 ml of methylene chloride each time. The extracts are combined, washed twice with 25 ml of saturated sodium hydrogen carbonate solution each time and with 25 ml of saturated sodium chloride solution, dried and concentrated to dryness by evaporation. 6-(N-benzyloxycarbonylamino)-2-methylene-hexanal is obtained in the form of a yellowish liquid.

4.0 g (15.3 mmol) of 6-(N-benzyloxycarbonylamino)-2-methylene-hexanal and 1.62 ml (16.8 mmol) of isocyanoacetic acid methyl ester are dissolved in 50 ml of toluene and added dropwise at 40° to a suspension of 0.12 g of 96.4% copper(I) oxide in 50 ml of toluene. The mixture is then stirred at room temperature for 2.5 hours, filtered, introduced into a column filled with 60 g of silica gel and extracted first with hexane/ethyl acetate (1:1) and then with ethyl acetate.

5-[6-(N-benzyloxycarbonylamino)hex-1-en-2-yl]-oxazoline-4-carboxylic acid methyl ester is obtained; oil.

9.4 g (26.1 mmol) of 5-[6-(N-benzyloxycarbonylamino)hex-1-en-2-yl]-oxazoline-4-carboxylic acid methyl ester are dissolved in 40 ml of tetrahydrofuran and 20 ml of water, a few drops of triethylamine are added and the mixture is heated under reflux for 18 hours. The solvent is removed under reduced pressure and the oil that remains is taken up in a total of 125 ml of methylene chloride, dried over magnesium sulfate and concentrated to dryness by evaporation. 8-(N-benzyloxycarbonylamino)-2-formylamino-3-hydroxy-4-methylene-octanoic acid methyl ester is obtained.

To 2.46 g (6.5 mmol) of 8-(N-benzyloxycarbonylamino)-2-formylamino-3-hydroxy-4-methylene-octanoic acid methyl ester in 25 ml of tetrahydrofuran there are added 5.5 ml (46 mmol) of hexa-1,5-diene and then, dropwise at −50°, 2.6 ml (32.5 mmol) of thionyl bromide. The mixture is stirred at from 0° to 5° for 2 hours, poured into 25 ml of ice-cold saturated sodium hydrogen carbonate solution and extracted twice with 20 ml of methylene chloride each time. The organic phase is washed with 10 ml of saturated sodium chloride solution, dried over magnesium sulfate and concentrated to dryness by evaporation. The resulting oil is purified by chromatography on silica gel with hexane/ethyl acetate (3:1). 8-(N-benzyloxycarbonylamino)-4-bromomethyl-2-formylamino-oct-3-enoic acid methyl ester is obtained.

5 ml of triethyl phosphite are added to 1.45 g (3.3 mmol) of 8-(N-benzyloxycarbonylamino)-4-bromomethyl-2-formylamino-oct-3-enoic acid methyl ester, and the mixture is heated at 75° for 8 hours with stirring. The excess triethyl phosphite is distilled off under reduced pressure to give an oily residue which is purified by chromatography on a silica gel column with first ethyl acetate and then ethyl acetate/methanol (9:1). 8-(N-benzyloxycarbonylamino)-4-diethylphosphonomethyl-2-formylamino-oct-3-enoic acid methyl ester is obtained.

EXAMPLE 4

1.77 g (4.5 mmol) of 4-diisopropylphosphonomethyl-2-formylamino-6-methoxy-hex-3-enoic acid ethyl ester are dissolved in 12 ml of dichloromethane, and 2.32 ml (18.0 mmol) of trimethylbromosilane are added dropwise at room temperature. The mixture is left to stand at room temperature for 22 hours, 12 ml of ethanol are added dropwise, the mixture is left to stand for a further 24 hours and is concentrated by evaporation in a rotary evaporator, the residue is dissolved in 10 ml of ethanol, and a mixture of 2 ml of propylene oxide and 2 ml of ethanol is added. A suspension forms, which is stirred for a further 2 hours at room temperature and for 2 hours with ice cooling, and is then filtered with suction. 2-amino-6-methoxy-4-phosphonomethyl-hex-3-enoic acid ethyl ester having a melting point of 242° (decomp.) is obtained.

The starting material can be prepared, for example, as follows:

19.7 g (193 mmol) of 4-methoxybutanal, 17.7 g (217 mmol) of dimethylammonium chloride and 17.0 ml (226 mmol) of 37% formaldehyde solution are heated at 100° for 3 hours with stirring. The mixture is allowed to cool and is extracted 3 times with diethyl ether. The organic phases are washed with saturated sodium chloride solution, combined, dried over sodium sulfate, filtered and concentrated to dryness by evaporation. 4-methoxy-2-methylenebutanal is obtained in the form of a yellowish oil which can be further reacted without further purification.

16.5 g (144.5 mmol) of 4-methoxy-2-methylenebutanal and 15.8 ml (144.5 mmol) of isocyanoacetic acid ethyl ester are dissolved in 145 ml of toluene, and 400 mg of copper(I) oxide are added. When the exothermic reaction has subsided, the mixture is stirred for a further 2 hours, filtered over Hyflo® and concentrated to dryness by evaporation. The residue is taken up in 145 ml of tetrahydrofuran, 33 ml of water are added, and the mixture is heated under reflux for 2 hours with stirring. The mixture is concentrated to dryness by evaporation, toluene is added, and the mixture is again concentrated by evaporation. Chromatography on silica gel with toluene/ethanol (95:5) as eluant yields 2-formylamino-3-hydroxy-6-methoxy-4-methylene-hexanoic acid ethyl ester in the form of a reddish-brown oil.

19.0 g (77.5 mmol) of 2-formylamino-3-hydroxy-6-methoxy-4-methylene-hexanoic acid ethyl ester are dissolved in 190 ml of 1,2-dichloroethane, and 7.20 ml (93.0 mmol) of thionyl bromide are added dropwise at room temperature. After 45 minutes, 100 ml of water are added and the mixture is stirred vigorously for 10 minutes. The organic phase is separated off, washed in succession with water, 1N potassium hydrogen carbonate solution and again with water, dried over sodium sulfate, filtered and concentrated by evaporation. 4-bromomethyl-2-formylamino-6-methoxy-hex-3-enoic acid ethyl ester is obtained in the form of a reddish-brown oil.

3.38 g (11.0 mmol) of 4-bromomethyl-2-formylamino-6-methoxy-hex-3-enoic acid ethyl ester and 12.0 ml (44 mmol) of triisopropyl phosphite (96%) are heated to 80° and stirred under a pressure of approximately 130 mbar for 18 hours. The excess triisopropyl phosphite is distilled off under reduced pressure and the evaporation residue is purified by chromatography on silica gel with ethyl acetate. 4-diisopropylphosphonomethyl-2-formylamino-6-methoxy-hex-3-enoic acid ethyl ester is obtained in the form of a yellowish oil.

EXAMPLE 5

0.98 g (3.5 mmol) of 2-amino-6-methoxy-4-phosphonomethyl-hex-3-enoic acid ethyl ester is heated under reflux in 7 ml of water for 17 hours. The reaction mixture is concentrated by evaporation and crystallised from a mixture of water and ethanol. 2-amino-6-methoxy-4-phosphonomethyl-hex-3-enoic acid having a melting point of 214° C. (decomp.) is obtained.

EXAMPLE 6

0.52 g (1.36 mmol) of 4-diisopropylphosphonomethyl-6-fluoro-2-formylamino-hex-3-enoic acid ethyl ester is dissolved in 3.5 ml of dichloromethane, and 0.7 ml (5.45 mmol) of trimethylbromosilane is added dropwise at room temperature. The mixture is left to stand at room temperature for 24 hours, 3.5 ml of ethanol are added dropwise, the mixture is left to stand for a further 24 hours and is concentrated by evaporation in a rotary evaporator, the residue is dissolved in 2.4 ml of ethanol, and a mixture of 0.6 ml of propylene oxide and 0.6 ml of ethanol is added. A suspension forms, which is stirred for a further 2 hours at room temperature and for 2 hours with ice cooling and is then filtered with suction. 2-amino-6-fluoro-4-phosphonomethyl-hex-3-enoic acid ethyl ester having a melting point of 222° (decomp.) is obtained.

The starting material can be prepared, for example, as follows:

2.4 g (26.6 mmol) of 4-fluorobutanal, 2.44 g (30.0 mmol) of dimethylammonium chloride and 2.34 ml (31.1 mmol) of 37% formaldehyde solution are heated at 100° for 2 hours with stirring. The mixture is allowed to cool and is extracted 3 times with diethyl ether. The organic phases are washed with saturated sodium chloride solution, combined, dried over sodium sulfate, filtered and concentrated to dryness by evaporation. 4-fluoro-2-methylenebutanal is obtained in the form of a yellowish oil which can be reacted further without further purification.

1.43 g (14.0 mmol) of 4-fluoro-2-methylenebutanal and 1.53 ml (14.0 mmol) of isocyanoacetic acid ethyl ester are dissolved in 14 ml of toluene, and 40 mg of copper(I) oxide are added. When the exothermic reaction has subsided, the mixture is stirred for a further 2 hours, filtered over Hyflo ® and concentrated to dryness by evaporation. The residue is taken up in 14 ml of tetrahydrofuran, 3.1 ml of water are added, and the mixture is heated under reflux for 2 hours with stirring. The mixture is concentrated to dryness by evaporation, toluene is added, and the mixture is again concentrated by evaporation. Chromatography on silica gel with toluene/ethyl acetate (1:1) as eluant yields 6-fluoro-2-formylamino-3-hydroxy-4-methylene-hexanoic acid ethyl ester in the form of a dark-yellow oil.

1.40 g (6.0 mmol) of 6-fluoro-2-formylamino-3-hydroxy-4-methylene-hexanoic acid ethyl ester are dissolved in 14 ml of 1,2-dichloroethane, and 0.56 ml (7.2 mmol) of thionyl bromide is added dropwise at room temperature. After 45 minutes, 12 ml of water are added and the mixture is stirred vigorously for 15 minutes. The organic phase is separated off, washed in succession with water, 1N potassium hydrogen carbonate solution and again with water, dried over sodium sulfate, filtered and concentrated by evaporation. 4-bromomethyl-6-fluoro-2-formylamino-hex-3-enoic acid ethyl ester is obtained in the form of a brownish-yellow oil.

1.43 g (4.82 mmol) of 4-bromomethyl-6-flouro-2-formylamino-hex-3-enoic acid ethyl ester and 5.3 ml (19 mmol) of triisopropyl phosphite (96%) are heated to 80° and stirred under a pressure of approximately 130 mbar for 18 hours. The excess triisopropyl phosphite is distilled off under reduced pressure and the evaporation residue is purified by chromatography on silica gel with ethyl acetate. 4-diisopropylphosphonomethyl-6-fluoro-2-formylamino-hex-3-enoic acid ethyl ester is obtained in the form of a yellowish oil.

EXAMPLE 7

0.5 g (1.86 mmol) of 2-amino-6-fluoro-4-phosphonomethyl-hex-3-enoic acid ethyl ester are heated under reflux in 4 ml of water for 17 hours. The reaction mixture is concentrated by evaporation and separated with water on a strongly acidic ion-exchanger (Dowex 50Wx8; H⊕ form). 2-amino-6-fluoro-4-phosphonomethyl-hex-3-enoic acid having a melting point of 160°-162° C. (decomp.) is obtained.

EXAMPLE 8

In a manner analogous to that described in Example 3, 2,10-diamino-4-phosphonomethyl-dec-3-enoic acid dihydrochloride, m.p. 126°, is obtained, starting from 8-aminooctan-1-ol.

EXAMPLE 9

8.63 g (15.2 mmol) of 10-(N-benzyloxycarbonylamino)-4-diisopropylphosphonomethyl-2-formylamino-dec-3-enoic acid ethyl ester are dissolved in 22 ml of dichloromethane, and 9.82 ml (75.9 mmol) of trimethylbromosilane are added dropwise at room temperature. The mixture is stirred at room temperature for 22 hours, 22 ml of absolute ethanol are then added dropwise, and the mixture is stirred for a further 22 hours and concentrated by evaporation in a rotary evaporator. 20 ml of toluene are poured over the residue, and the mixture is concentrated by evaporation in vacuo. This operation is repeated a further three times. The resulting pale yellow foam is dissolved in 150 ml of absolute ethanol, and a solution of 7.5 ml of propylene oxide in 7.5 ml of ethanol is added dropwise within a period of 90 minutes. A crystalline suspension forms, which is stirred overnight at room temperature. The product is filtered off and washed with ethanol and ether. Drying under a high vacuum at room temperature yields 4.70 g of crude product in the form of pale yellow crystals. For further purification, the product is stirred with 46 ml of water. After a small amount (0.33 g) of undissolved material has been filtered off, the clear pale yellow filtrate is completely concentrated by evaporation in vacuo. 20 ml of ethanol and 20 ml of toluene are added to the residue, and the mixture is again concentrated to dryness by evaporation. This operation is repeated twice more using toluene. After drying under a high vacuum, the residue is suspended in 150 ml of absolute ethanol, and a 5-normal solution of hydrogen chloride gas in ethanol is added dropwise, with stirring, until the mixture gives an acid reaction to Congo red. A mixture of 7.4 ml of propylene oxide in 7.4 ml of ethanol is added dropwise to the resulting clear solution within a period of one hour. A crystalline suspension forms, which is stirred for a further 15 hours and then filtered with suction. After washing with ethanol and ether, the product is dried under a high vacuum at 50° for 48 hours, yielding 2.86 g of 2,10-diamino-4-phosphonomethyl-dec-3-enoic acid ethyl ester, which begins to sinter at 157° and melts at 194° with decomposition.

This product contains as impurities approximately from 5 to 10% by weight of the corresponding compound that is N-benzylated in the 10-position and of the N-(2-hydroxy)propylated compound.

The starting material is prepared as follows:

In a manner analogous to that described in Example 3, 8-(N-benzyloxycarbonylamino)-2-methyleneoctanal is obtained, starting from 8-aminooctan-1-ol, via 8-(N-benzyloxycarbonylamino)octan-1-ol and 8-(N-benzyloxycarbonylamino)octanal.

15.30 g (52.9 mmol) of 8-(N-benzyloxycarbonylamino)-2-methyleneoctanal and 7.37 ml (67.4 mmol) of isocyanoacetic acid ethyl ester are dissolved in 78 ml of toluene and added dropwise under argon, within a period of 75 minutes, to a suspension of 0.30 g of copper(I) oxide in 76 ml of toluene. The mixture is then stirred for 90 minutes at 30°, cooled to room temperature and filtered, and the clear, bright red filtrate is introduced into a column filled with 250 g of silica gel (particle size 0.04–0.063 mm) and eluted with hexane/ethyl acetate (2:1). Concentration of the suitable fractions by evaporation yields 8.15 g of 5-[8-(N-benzyloxycarbonylamino)oct-1-en-2-yl]-oxazoline-4-carboxylic acid ethyl ester in the form of a colourless honey.

8.15 g (20.25 mmol) of 5-[8-(N-benzyloxycarbonylamino)oct-1-en-2-yl]-oxazoline-4-carboxylic acid ethyl ester are heated under reflux in 40 ml of tetrahydrofuran and 20 ml of water for 4 hours with stirring. The reaction mixture is concentrated to dryness by evaporation in vacuo at 45°, and the honey-like residue is concentrated by evaporation twice more after the addition of toluene. The crude product is dissolved in dichloromethane, dried with sodium sulfate, filtered and concentrated by evaporation. Drying under a high vacuum at room temperature yields 9.03 g of 10-(N-benzyloxycarbonylamino)-2-formylamino-3-hydroxy-4- methylene-decanoic acid ethyl ester in the form of a yellowish honey.

To 13.70 g (32.60 mmol) of crude 10-(N-benzyloxycarbonylamino)-2-formylamino-3-hydroxy-4-methylene-decanoic acid ethyl ester in 137 ml of tetrahydrofuran there are added, under argon, 18.5 ml (156.4 mmol) of hexa-1,5-diene and then, dropwise at 10° within a period of 15 minutes, 6.1 ml (78.2 mmol) of thionyl bromide. The mixture is stirred for one hour at 10° and for 2 hours at room temperature and is then poured into 200 ml of ice-cold saturated sodium hydrogen carbonate solution; the organic phase is separated off and re-extracted once with dichloromethane. The organic phases are washed with ice-cold 0.5-normal sodium hydrogen carbonate solution and then with saturated sodium chloride solution, dried over sodium sulfate and concentrated to dryness by evaporation in vacuo at 40°. 64 ml (260 mmol) of triisopropyl phosphite (96%) are added immediately to the resulting crude 10-(N-benzyloxycarbonylamino)-4-bromomethyl-2-formylaminodec-3-enoic acid ethyl ester (27 g, yellow honey), and the mixture is stirred for 17 hours at 80° under a pressure of approximately 100 mbar, the isopropyl bromide that forms being captured in a cold trap ($CO_2$). The excess triisopropyl phosphite is then distilled off under reduced pressure and the evaporation residue (23 g) is purified by chromatography on a column filled with 650 mg of silica gel (0.04-0.063 mm) with ethyl acetate/methanol (95:5). 8.73 g of 10-(N-benzyloxycarbonylamino)-4-diisopropylphosphonomethyl-2-formylaminodec-3-enoic acid ethyl ester are obtained in the form of a yellowish honey.

EXAMPLE 10

2.25 g (6.98 mmol) of 2,10-diamino-4-phosphonomethyl-dec-3-enoic acid ethyl ester are dissolved under argon in 45 ml of 2-normal hydrochloric acid and stirred for 17 hours at a bath temperature of 120°. The clear, pale brown solution is concentrated by evaporation in a rotary evaporator. The residue is dissolved in 20 ml of ethanol and, after the addition of 30 ml of toluene, concentrated by evaporation in vacuo. This operation is repeated a further three times. The resulting beige foam is dissolved in 75 ml of absolute ethanol, and a solution of 15 ml of propylene oxide in 15 ml of ethanol is added dropwise within a period of 35 minutes. The crystalline suspension that forms, which has a pH of 3, is filtered off after 1½ hours' stirring and washed thoroughly with ethanol and ether. Drying in vacuo yields 1.65 g of beige crude product, which is dissolved in the minimum amount of water (about 2 ml) and chromatographed on a column filled with 67 g of reversed-phase silica gel (Opti-Up $C_{12}$, particle size 40 μm), using pure water as eluant, at a slight overpressure (0.2 bar). A pure fraction, Rf value on silica gel=0.37 with n-propanol/water/pyridine/acetic acid (15:12:10:3) as eluant, and several mixed fractions containing a by-product of Rf value=0.48 are obtained. Chromatography of those mixed fractions again and purification of the pure fractions, followed by lyophilisation from water, yield 2,10-diamino-4-phosphonomethyl-dec-3-enoic acid hemi-hydrochloride hydrate in the form of an amorphous glass which slowly sinters at 134° and above and decomposes at 149° with foaming.

EXAMPLE 11

4.3 g (9.9 mmol) of 7-acetoxy-4-diisopropylphosphonomethyl-2-formylamino-hept-3-enoic acid ethyl ester are dissolved in 25 ml of dichloromethane, and 5.1 ml (39.5 mmol) of trimethylbromosilane are added dropwise at room temperature. The mixture is left to stand at room temperature for 24 hours, 25 ml of ethanol are added dropwise, the mixture is left to stand for a further 24 hours and is concentrated by evaporation, the residue is dissolved in 25 ml of ethanol, and a mixture of 25 ml of propylene oxide and 25 ml of ethanol is added dropwise. A suspension forms, which is stirred for one hour at room temperature and for one hour in an ice bath and is then filtered with suction. Drying yields 2-amino-7-hydroxy-4-phosphonomethyl-hept-3-enoic acid ethyl ester having a melting point of 210° C. (decomp.).

The starting material can be prepared, for example, as follows:

10 g (69.4 mmol) of 5-acetoxypentanal, 6.37 g (78.2 mmol) of dimethylammonium chloride and 6.1 ml (81.2 mmol) of 37% formaldehyde solution are refluxed for 1½ hours (bath temperature ~110° C.) with stirring. The mixture is allowed to cool and is extracted three times with ether; the organic phases are combined, dried over $MgSO_4$, filtered and concentrated by evaporation. 5-acetoxy-2-methylenepentanal is obtained in the form of a yellowish oil which can be reacted without further purification.

9.6 g (61.5 mmol) of 5-acetoxy-2-methylenepentanal and 7.38 ml (67.6 mmol) of isocyanoacetic acid ethyl ester are placed in 70 ml of toluene at room temperature, and 250 mg of copper(I) oxide are added. When the exothermic reaction has subsided, the mixture is stirred for a further one hour and is filtered over Hyflo ® and concentrated by evaporation. The residue is taken up in 50 ml of tetrahydrofuran, 10 ml of water are added, and the mixture is refluxed for 3 hours. The mixture is concentrated to dryness by evaporation, toluene is added, and the mixture is again concentrated by evaporation. Chromatography on silica gel with toluene/ethyl acetate (4:1) yields 7-acetoxy-2-formylamino-3-hydroxy-4-methylene-heptanoic acid ethyl ester in the form of an orange oil.

5.9 g (20.5 mmol) of 7-acetoxy-2-formylamino-3-hydroxy-4-methylene-heptanoic acid ethyl ester are dissolved in 60 ml of dichloromethane, and 1.9 ml (24.6 mmol) of thionyl bromide are added dropwise at room temperature. After one hour, 40 ml of water are added and the mixture is stirred vigorously for 10 minutes. The organic phase is separated off, washed in succession with water, 1N $KHCO_3$ solution and again with water, dried over $MgSO_4$, filtered and concentrated by evaporation. 7-acetoxy-4-bromomethyl-2-formylamino-hept-3-enoic acid ethyl ester is obtained in the form of a brown oil, which is reacted further in the crude state.

6.1 g (17.4 mmol) of 7-acetoxy-4-bromomethyl-2-formylaminohept-3-enoic acid ethyl ester and 19.1 ml (69.6 mmol) of triisopropyl phosphite (90%) are heated to 80° C. and stirred under a pressure of approximately 130 mbar for 18 hours. The excess triisopropyl phosphite is distilled off and the residue is purified on silica gel with ethyl acetate. 7-acetoxy-4-diisopropylphosphonomethyl-2-formylamino-hept-3-enoic acid ethyl ester is obtained in the form of a yellow oil.

EXAMPLE 12

1.1 g (3.9 mmol) of 2-amino-7-hydroxy-4-phosphonomethyl-hept-3-enoic acid ethyl ester in 8 ml of water are stirred at 130° C. for 18 hours in a bomb tube. The dark reaction solution is treated with activated carbon and filtered over Hyflo ®. The colourless filtrate is concentrated to ~3 ml, and ~25 ml of ethanol are added. The resulting suspension is filtered with suction and dried under a high vacuum at 50° C. 2-amino-7-hydroxy-4-phosphonomethyl-hept-3-enoic acid having a melting point from 190° C. and above (decomp.) is obtained.

EXAMPLE 13

8.2 g (18.9 mmol) of 6-(N-acetyl-N-methylamino)-4-diisopropylphosphonomethyl-2-formylamino-hex-3-enoic acid ethyl ester are dissolved in 40 ml of dichloromethane, and 9.8 ml (75.6 mmol) of trimethylbromosilane are added dropwise at room temperature. The mixture is left to stand at room temperature for 24 hours, 40 ml of ethanol are added dropwise, the mixture is left to stand for a further 24 hours and is concentrated by evaporation, the residue is dissolved in 40 ml of ethanol, and a mixture of 40 ml of propylene oxide and 40 ml of ethanol is added dropwise. A suspension forms, which is stirred for a further one hour at room temperature and for one hour at 0° and is then filtered with suction. Drying yields 6-(N-acetyl-N-methylamino)-2-amino-4-phosphonomethyl-hex-3-enoic acid ethyl ester having a melting point of 222°-223° C. (decomp.).

The starting material can be prepared, for example, as follows:

35.8 g (0.2 mol) of 4-aminobutyraldehyde-diethylacetal (90%) are dissolved in 600 ml of dichloromethane, 300 ml of saturated sodium hydrogen carbonate solution are added, and the mixture is cooled to 0° C. 17 ml (0.24 mol) of acetyl chloride are added dropwise at 0°-5° C., and the mixture is stirred for a further 6 hours at 0°-5° C. The organic phase is separated off and the aqueous phase is extracted twice more with dichloromethane. The organic phases are combined, dried over MgSO4, filtered and concentrated by evaporation in a rotary evaporator. The residue is purified by chromatography on silica gel with ethyl acetate. 4-(N-acetylamino)-butyraldehyde-diethylacetal is obtained in the form of a yellowish oil.

35 g (172.2 mmol) of 4-(N-acetylamino)butyraldehyde-diethylacetal are dissolved in 180 ml of dimethylformamide, 8.3 g (206.6 mmol) of sodium hydride dispersion (60% in mineral oil) are added in portions, and the mixture is stirred at room temperature for 45 minutes. 12.9 ml (206.6 mmol) of methyl iodide in 20 ml of dimethylformamide are then added, and the mixture is subsequently stirred at room temperature for 4 hours. Water/ice is added to the reaction mixture, and the batch is extracted three times with ethyl acetate. The organic phases are washed with water and saturated sodium chloride solution, combined, dried over MgSO4, filtered and concentrated by evaporation. The residue is distilled under a high vacuum. 4-(N-acetyl-N-methylamino)butyraldehydediethylacetal is obtained in the form of a colourless oil, b.p.$_{0.1}$=92°-94°.

30 g (138.2 mmol) of 4-(N-acetyl-N-methylamino)-butyraldehydediethylacetal, 12.6 g (154.4 mmol) of dimethylammonium chloride and 12.1 ml (161.7 mmol) of 37% formaldehyde solution are refluxed for 45 minutes with stirring. The mixture is allowed to cool and is extracted three times with dichloromethane. The organic phases are combined, dried over MgSO4, filtered and concentrated by evaporation. 4-(N-acetyl-N-methylamino)-2-methylene-butyraldehyde is obtained in the form of a yellowish oil which can be reacted without further purification. 19.9 g (128.3 mmol) of 4-(N-acetyl-N-methylamino)-2-methylene-butanal and 15.4 ml (141.1 mmol) of isocyanoacetic acid ethyl ester are placed at room temperature in 80 ml of toluene, and 500 mg of copper(I) oxide are added. When the exothermic reaction has subsided, the mixture is stirred for a further one hour at room temperature, filtered over Hyflo ® and concentrated by evaporation. The residue is taken up in 60 ml of tetrahydrofuran, 20 ml of water are added, and the mixture is refluxed for 4 hours. The mixture is concentrated by evaporation, toluene is added, and the mixture is again concentrated by evaporation. Chromatography on silica gel with ethyl acetate/isopropanol (7:1) yields 6-(N-acetyl-N-methylamino)-2-formylamino-3-hydroxy-4-methylene-hexanoic acid ethyl ester in the form of a yellowish oil.

15.8 g (55.2 mmol) of 6-(N-acetyl-N-methylamino)-2-formylamino-3-hydroxy-4-methylene-hexanoic acid ethyl ester are dissolved in 150 ml of dichloromethane, and 5.1 ml (66.2 mmol) of thionyl bromide are added dropwise at room temperature. After one hour, 100 ml of water are added and the mixture is stirred vigorously for 10 minutes. The organic phase is separated off, washed in succession with water, 1N KHCO3 solution and again with water, dried over MgSO4, filtered and concentrated by evaporation. 6-(N-acetyl-N-methylamino)-4-bromomethyl-2-formylamino-hex-3-enoic acid ethyl ester is obtained in the form of a yellowish-orange oil which is reacted further in the crude state.

16.0 g (45.8 mmol) of 6-(N-acetyl-N-methylamino)-4-bromomethyl-2-formylamino-hex-3-enoic acid ethyl ester and 50.3 ml (183.3 mmol) of triisopropyl phosphite (90%) are heated to 80° and stirred under a pressure of approximately 130 mbar for 18 hours. The excess triisopropyl phosphite is distilled off and the residue is purified by chromatography on silica gel with ethyl acetate/isopropanol (7:2). 6-(N-acetyl-N-methylamino)-4-diisopropylphosphonomethyl-2-formylamino-hex-3-enoic acid ethyl ester is obtained in the form of a yellow oil.

EXAMPLE 14

3.3 g (6.82 mmol) of 6-benzoyloxy-4-diisopropylphosphonomethyl-2-formylamino-hex-3-enoic acid ethyl ester are dissolved in 20 ml of dichloromethane, and 3.52 ml (27.3 mmol) of trimethylbromosilane are added dropwise at room temperature. The mixture is left to stand at room temperature for 22 hours, 20 ml of ethanol are added dropwise, the mixture is left to stand for a further 22 hours and is concentrated by evaporation, the residue is dissolved in 20 ml of ethanol, and a mixture of 20 ml of propylene oxide and 20 ml of ethanol is added dropwise. A suspension forms, which is stirred for one hour at room temperature and for one hour at 0° C. and is then filtered with suction. Drying yields 2-amino-6-benzoyloxy-2-amino-4-phosphonomethyl-hex-3-enoic acid ethyl ester having a melting point of 236°-237° C. (decomp.).

The starting material can be prepared, for example, as follows:

10 g (52 mmol) of 4-benzoyloxybutanal, 4.78 g (58.6 mmol) of dimethylammonium chloride and 4.6 ml (60.8 mmol) of formaldehyde solution (37%) are refluxed for one hour with stirring (bath temperature ~110° C.). The mixture is allowed to cool and is extracted three times with ether; the organic phases are combined, washed with saturated sodium chloride solution, dried over MgSO$_4$, filtered and concentrated by evaporation. 4-benzoyloxy-2-methylenebutanal is obtained in the form of a yellowish oil which can be reacted without further purification.

10 g (49 mmol) of 4-benzoyloxy-2-methylenebutanal and 5.3 ml (49 mmol) of isocyanoacetic acid ethyl ester are placed at room temperature in 70 ml of toluene, and 200 mg of copper(I) oxide are added. When the exothermic reaction has subsided, the mixture is stirred for a further one hour, filtered over Hyflo ® and concentrated by evaporation. The residue is taken up in 50 ml of tetrahydrofuran, 10 ml of water are added, and the mixture is refluxed for 3 hours. The mixture is concentrated by evaporation, toluene is again added, and the mixture is again concentrated by evaporation. Chromatography on silica gel with toluene/ethyl acetate (3:2) yields 6-benzoyloxy-2-formylamino-3-hydroxy-4-methylene-hexanoic acid ethyl ester in the form of a brown oil.

8 g (23.9 mmol) of 6-benzoyl-2-formylamino-3-hydroxy-4-methylene-hexanoic acid ethyl ester are dissolved in 80 ml of dichloromethane, and 2.22 ml (28.6 mmol) of thionyl bromide are added dropwise at room temperature. After 2 hours, 60 ml of water are added and the mixture is stirred vigorously for 10 minutes. The organic phase is separated off, washed in succession with water, 1N KHCO$_3$ solution and again with water, dried over MgSO$_4$, filtered and concentrated by evaporation. 6-benzoyloxy-4-bromomethyl-2-formylamino-hex-3-enoic acid ethyl ester is obtained in the form of a brown oil which is reacted further in the crude state.

8.4 g (21 mmol) of 6-benzoyloxy-4-bromomethyl-2-formylamino-hex-3-enoic acid ethyl ester and 23 ml (84 mmol) of triisopropyl phosphite (90%) are heated to 80° C. and stirred under a pressure of ~130 mbar for 18 hours. The excess triisopropyl phosphite is distilled off and the residue is purified by chromatography on silica gel with ethyl acetate. 6-benzoyloxy-4-diisopropylphosphonomethyl-2-formylamino-hex-3-enoic acid ethyl ester is obtained in the form of a brown oil.

EXAMPLE 15

4.0 g (8.51 mmol) of 6-benzyloxy-4-diisopropylphosphonomethyl-2-formylamino-hex-3-enoic acid ethyl ester are dissolved in 24 ml of dichloromethane, and 4.4 ml (34 mmol) of trimethylbromosilane are added dropwise at room temperature. The mixture is left to stand at room temperature for 22 hours, 24 ml of ethanol are added dropwise and the mixture is left to stand for a further 24 hours and is concentrated by evaporation in a rotary evaporator, the residue is dissolved in 24 ml of ethanol, and a mixture of 24 ml of propylene oxide and 24 ml of ethanol is added dropwise. A suspension forms, which is stirred for a further one hour at room temperature and for one hour at 0° and is then filtered with suction. Drying yields 2.2 g of a white crystalline product which is a mixture of 2-amino-6-benzyloxy-4-phosphonomethyl-hex-3-enoic acid ethyl ester and 2-amino-6-benzyloxy-4-phosphonomethyl-hex-3-enoic acid. To obtain a uniform product, that mixture is hydrolysed overnight at room temperature with 20 ml of N-sodium hydroxide solution in 30 ml of ethanol, acidified with N-hydrochloric acid and neutralised with propylene oxide. Since the product crystallises poorly, it is concentrated by evaporation in a rotary evaporator, the residue is filtered in water over 20 g of silica gel, and the fractions containing the desired product are concentrated by evaporation in a rotary evaporator. The residue is dissolved with 10 ml of tert.-butanol/water (1:1) and freeze-dried. 2-amino-6-benzyloxy-4-phosphonomethyl-hex-3-enoic acid is obtained in the form of a lyophilisate.

The starting material can be prepared, for example, as follows:

6 g (0.2 mol) of a sodium hydride dispersion (80% in white oil) are placed at room temperature in 120 ml of absolute dimethylformamide, and 22.2 ml (0.25 mol) of 1,4-butanediol are added dropwise. When the addition is complete, the mixture is stirred for a further 30 minutes at room temperature. 23.1 ml (0.2 mol) of benzyl chloride are then slowly added dropwise, a slight exothermic reaction being observed. The reaction mixture is stirred overnight at room temperature, water/ice is added, and the mixture is extracted twice with ether. The organic phases are washed with water and with saturated sodium chloride solution, combined, dried over MgSO$_4$, filtered and concentrated by evaporation. The residue is subjected to fractional distillation under a water-jet vacuum over a 10 cm Vigreux column. 4-benzyloxybutanol is obtained, b.p.$_{22}$=161°-162°.

36.6 g (170 mmol) of pyridinium chlorochromate are placed at room temperature in 120 ml of dichloromethane under N$_2$, and a solution of 20.4 g (113 mmol) of 4-benzyloxybutanol in 20 ml of dichloromethane is added. The reaction mixture rapidly becomes dark and the reaction is slightly exothermic. The reaction mixture is stirred at room temperature for 3½ hours. The supernatant dichloromethane phase is decanted off and concentrated by evaporation in a rotary evaporator. The residue is filtered over 100 g of silica gel. The product fractions are concentrated by evaporation in a rotary evaporator and distilled under a high vacuum over a 10 cm Vigreux column. 4-benzyloxybutanal is obtained, b.p.$_{0.1}$=72°-73°.

8.0 g (44.9 mmol) of 4-benzyloxybutanal, 4.12 g (50.6 mmol) of dimethylammonium chloride and 3.95 ml (52.6 mmol) of 37% formaldehyde solution are kept at a bath temperature of 110° for one hour with stirring. The mixture is allowed to cool and is extracted three times with ether. The organic phases are washed with saturated sodium chloride solution, combined, dried over MgSO$_4$, filtered and concentrated by evaporation. 4-benzyloxy-2-methylenebutanal is obtained in the form of a yellowish oil which can be reacted further without further purification.

8.0 g (42 mmol) of 4-benzyloxy-2-methylenebutanal and 4.57 ml (42 mmol) of isocyanoacetic acid ethyl ester are placed in 60 ml of toluene, and 200 mg of copper(I) oxide are added. When the exothermic reaction has subsided, the mixture is stirred for a further 2 hours, filtered over Hyflo ® and concentrated by evaporation. The residue is taken up in 50 ml of tetrahydrofuran, 10 ml of water are added, and the mixture is refluxed for 3 hours. The mixture is concentrated to dryness by evaporation, toluene is added, and the mixture is again concentrated by evaporation. Chromatography on silica gel with toluene/ethyl acetate (3:2) as eluant yields 6-benzyloxy-2-formylamino-3-hydroxy-4-methylene-hexanoic acid ethyl ester in the form of a reddish-brown oil.

7.0 g (21.8 mmol) of 6-benzyloxy-2-formylamino-3-hydroxy-4-methylene-hexanoic acid ethyl ester are dissolved in 70 ml of dichloromethane, and 2.0 ml (26.1 mmol) of thionyl bromide are added dropwise at room temperature. After 2 hours, 40 ml of water are added and the mixture is stirred vigorously for 10 minutes. The organic phase is separated off, washed in succession with water, N—KHCO₃ solution and again with water, dried over
MgSO₄, filtered and concentrated by evaporation. 6-benzyloxy-4-bromomethyl-2-formylamino-hex-3-enoic acid ethyl ester is obtained in the form of a reddish-brown oil which can be reacted further without purification.

7.9 g (20.5 mmol) of 6-benzyloxy-4-bromomethyl-2-formylamino-hex-3-enoic acid ethyl ester and 22.5 ml (82.2 mmol) of triisopropyl phosphite (90%) are heated to 80° and stirred under a pressure of approximately 130 mbar for 18 hours. The excess triisopropyl phosphite is distilled off in a rotary evaporator and the residue is purified by chromatography on silica gel with ethyl acetate. 6-benzoyl-4-diisopropylphosphonomethyl-2-formylamino-hex-3-enoic acid ethyl ester is obtained in the form of a yellowish oil.

EXAMPLE 16

3.15 g (6.84 mmol) of 4-(1-acetylpiperidin-4-yl)-5-diisopropylphosphono-2-formylamino-pent-3-enoic acid ethyl ester are dissolved in 17 ml of dichloromethane, and 3.54 ml (27.3 mmol) of trimethylbromossilane are added dropwise at room temperature. The mixture is left to stand room at temperature for 16 hours, 17 ml of ethanol are added dropwise, the mixture is left to stand for a further 18 hours and is concentrated by evaporation in a rotary evaporator, the residue is dissolved in 12 ml of ethanol, and a mixture of 3 ml of propylene oxide and 3 ml of ethanol is added. A suspension forms, which is stirred for a further 2 hours at room temperature and for 2 hours with ice cooling and is then filtered with suction. 2-amino-4-(1-acetylpiperidin-4-yl)-5-phosphono-pent-3-enoic acid ethyl ester having a melting point of 225° (decomp.) is obtained.

The starting material can be prepared, for example, as follows:

3.95 g (23.3 mmol) of 2-(1-acetylpiperidin-4-yl)ethanol, 2.12 g (26.3 mmol) of dimethylammonium chloride and 3 ml (40 mmol) of 37% formaldehyde solution are heated at 110° C. for 2 hours with stirring. The mixture is allowed to cool and is extracted several times with diethyl ether. The organic phases are combined, washed with saturated sodium chloride solution, dried over sodium sulfate, filtered and concentrated to dryness by evaporation. 2-(1-acetylpiperidin-4-yl)propenal is obtained in the form of a yellowish oil which can be further reacted without further purification.

2.9 g (16.0 mmol) of 2-(1-acetylpiperidin-4-yl)propenal and 1.75 ml (16 mmol) of isocyanoacetic acid ethyl ester are dissolved in 13 ml of toluene, and 46 mg of copper(I) oxide are added. When the exothermic reaction has subsided, the mixture is stirred for a further 2 hours, filtered over Hyflo ® and concentrated to dryness by evaporation. The residue is taken up in 13 ml of tetrahydrofuran, 6 ml of water are added, and the mixture is heated under reflux for 2 hours with stirring. The mixture is concentrated to dryness by evaporation, toluene is added, and the mixture is again concentrated by evaporation. Chromatography on silica gel with ethyl acetate/methanol (9:1) as eluant yields 4-(1-acetylpiperidin-4-yl)-2-formylamino-3-hydroxy-pent-4-enoic acid ethyl ester in the form of a yellowish-brown oil.

3.3 g (10.5 mmol) of 4-(1-acetylpiperidin-4-yl)-2-formylamino-3-hydroxy-pent-4-enoic acid ethyl ester are dissolved in 25 ml of 1,2-dichloroethane, and 0.98 ml (12.6 mmol) of thionyl bromide are added dropwise at room temperature. After 1½ hours, 20 ml of water are added and the mixture is stirred vigorously for 15 minutes. The organic phase is separated off, washed in succession with water, N-potassium hydrogen carbonate solution and again with water, dried over sodium sulfate, filtered and concentrated by evaporation. 4-(1-acetylpiperidin-4-yl)-5-bromo-2-formylamino-pent-3-enoic acid ethyl ester is obtained in the form of a reddish-brown oil.

2.68 g (7.14 mmol) of 4-(1-acetylpiperidin-4-yl)-5-bromo-2-formylamino-pent-3-enoic acid ethyl ester and 7.5 ml (28.5 mmol) of triisopropyl phosphite (90%) are heated to 80° and stirred under a pressure of approximately 130 mbar for 18 hours. The excess triisopropyl phosphite is distilled off under reduced pressure and the evaporation residue is purified by chromatography on silica gel with ethyl acetate/methanol (9:1). 4-(1-acetylpiperidin-4-yl)-5-diisopropylphosphono-2-formylamino-pent-3-enoic acid ethyl ester is obtained in the form of a yellowish oil.

EXAMPLE 17

1 g (2.17 mmol) of 4-(1-acetylpiperidin-4-yl)-5-diisopropylphosphono-2-formylamino-pent-3-enoic acid ethyl ester is heated under reflux in 20 ml of 6N hydrochloric acid for 8 hours. After concentration by evaporation, the residue is dissolved in 25 ml of ethanol. 3 ml of propylene oxide are then added, the mixture is stirred for 2 hours at room temperature and for one hour with ice cooling, and then the suspension that has formed is filtered off with suction. 2-amino-4-(piperidin-4-yl)-5-phosphono-pent-3-enoic acid having a melting point of 212° (decomp.) is obtained.

EXAMPLE 18

0.68 g (1.49 mmol) of 5-benzyloxy-4-diisopropylphosphonomethyl-2-formylamino-pent-3-enoic acid ethyl ester is dissolved in 10 ml of dichloromethane, and 0.8 ml (6 mmol) of trimethylbromosilane is added dropwise at room temperature. The mixture is left to stand at room temperature for 6 hours, 10 ml of ethanol are added dropwise, the mixture is left to stand for a further 18 hours and is concentrated by evaporation, the residue is dissolved in 5 ml of ethanol, and a mixture of 5 ml of propylene oxide and 5 ml of ethanol is added dropwise. A suspension forms, which is stirred at room temperature for 2 hours and is then filtered with suction. Drying yields 2-amino-5-benzyloxy-4-phosphonomethyl-pent-3-enoic acid ethyl ester having a melting point of 218°–220° (decomp.).

The starting material can be prepared, for example, as follows:

3.0 g (62.4 mmol) of 50% sodium hydride dispersion in mineral oil are placed in 50 ml of tetrahydrofuran and 40 ml of dimethylformamide, a solution of 10.0 g (62.4 mmol) of 3-hydroxy-2-methylenepropionaldehyde-diethylacetal in 10 ml of tetrahydrofuran is slowly added dropwise at 0°, and the mixture is stirred at 0° for 2 hours. The mixture is diluted with 15 ml of tetrahydrofuran and 10 ml of dimethylformamide and stirred at room temperature for a further 2 hours. 7.2 ml (62.4 mmol) of benzyl chloride in 10 ml of dimethylformamide are then added at 0°, and the mixture is stirred at room temperature for 18 hours. Water is added to the reaction mixture, which is then extracted three times with ethyl acetate, and the organic phases are washed with saturated sodium chloride solution. The organic phases are combined, dried over Na$_2$SO$_4$, filtered and concentrated by evaporation. The residue is chromatographed on silica gel with methylene chloride, yielding 3-benzyloxy-2-methylenepropionaldehyde-diethylacetal in the form of a pale yellowish liquid.

4.8 g (19.1 mmol) of 3-benzyloxy-2-methylenepropionaldehyde-diethylacetal and 0.36 g (1.9 mmol) of p-toluenesulfonic acid monohydrate are stirred for 3 hours in 60 ml of acetone. The mixture is diluted with 400 ml of methylene chloride, extracted with N—KHCO$_3$ solution and saturated sodium chloride solution, dried over Na$_2$SO$_4$, filtered and concentrated by evaporation. The 3-benzyloxy-2-methylenepropanol that remains (yellow liquid) is placed at room temperature, without further purification, together with 2.1 ml (19 mmol) of isocyanoacetic acid ethyl ester, in 25 ml of toluene, and 50 mg of copper(I) oxide are added. When the exothermic reaction has subsided, the mixture is stirred for a further one hour at room temperature, filtered over Hyflo ® and concentrated by evaporation. The residue is taken up in 25 ml of tetrahydrofuran, 5 ml of water are added, and the mixture is refluxed for 4 hours. The mixture is concentrated by evaporation, toluene is added, and the mixture is again concentrated by evaporation. Chromatography on silica gel with toluene/ethyl acetate (1:1) and subsequent crystallisation from diethyl ether yield 5-benzyloxy-2-formylamino-3-hydroxy-4-methylene-pentanoic acid ethyl ester having a melting point of 112°–114° C.

1.0 g (3.25 mmol) of 5-benzyloxy-2-formylamino-3-hydroxy-4-methylene-pentanoic acid ethyl ester are suspended in 30 ml of 1,2-dichloroethane, and 0.38 ml (4.9 mmol) of thionyl chloride is added dropwise at room temperature. After 45 minutes, 20 ml of water are added to the yellow solution, and the mixture is stirred vigorously for 15 minutes. The organic phase is separated off, washed with saturated sodium chloride solution, dried over Na$_2$SO$_4$, filtered and concentrated by evaporation.

5-benzyloxy-4-bromomethyl-2-formylamino-pent-3-enoic acid ethyl ester is obtained in the form of a yellowish oil which is reacted further in the crude state.

1.14 g (3.1 mmol) of 5-benzyloxy-4-bromomethyl-2-formylamino-pent-3-enoic acid ethyl ester and 10 ml (38.5 mmol) of triisopropyl phosphite (95%) are heated to 80° C. and stirred under a pressure of approximately 130 mbar for 3½ hours. The excess triisopropyl phosphite is distilled off and the residue is purified by chromatography on silica gel with ethyl acetate. 5-benzyloxy-4-diisopropylphosphonomethyl-2-formylamino-pent-3-enoic acid ethyl ester is obtained in the form of a yellowish oil.

EXAMPLE 19

1.10 g (2.8 mmol) of 5-ethoxy-4-diisopropylphosphonomethyl-2-formylamino-pent-3-enoic acid ethyl ester are dissolved in 20 ml of dichloromethane, and 1.6 ml (12.3 mmol) of trimethylsilane are added dropwise at room temperature. The mixture is left to stand at room temperature for 7 hours, 20 ml of ethanol are added, the mixture is left to stand for a further 15 hours and is concentrated by evaporation, the residue is dissolved in 10 ml of ethanol, and a mixture of 10 ml of propylene oxide and 10 ml of ethanol is added dropwise. A suspension forms, which is stirred at room temperature for 2 hours and is then filtered with suction. Drying yields 5-ethoxy-2-amino-4-phosphonomethyl-pent-3-enoic acid ethyl ester having a melting point of 217°–218° C. (decomp.).

The starting material can be prepared, for example, as follows:

50 g (283 mmol) of 3-ethoxypropionaldehyde-diethylacetal, 27.3 g (335 mmol) of dimethylammonium chloride and 30 ml (392 mmol) of 36% formaldehyde solution are heated at 110° C. for 2 hours with stirring. The mixture is allowed to cool and is extracted three times with diethyl ether. The organic phases are washed with saturated sodium chloride solution, combined, dried over sodium sulfate, filtered and concentrated to dryness by evaporation. 2-ethoxypropanol is obtained in the form of a yellow liquid which can be reacted further without further purification.

4.2 g (36.1 mmol) of 2-ethoxypropanol and 4.4 ml (40 mmol) of isocyanoacetic acid ethyl ester are dissolved in 50 ml of toluene, and 200 mg of copper(I) oxide are added. When the exothermic reaction has subsided, the mixture is stirred for a further one hour, filtered over Hyflo ® and concentrated to dryness by evaporation. The residue is taken up in 50 ml of tetrahydrofuran, 12 ml of water are added, and the mixture is heated under reflux for one hour with stirring. The mixture is concentrated to dryness by evaporation, toluene is added, and the mixture is again concentrated by evaporation. Chromatography on silica gel with toluene/isopropanol (9:1) as eluant yields 5-ethoxy-2-formylamino-3-hydroxy-4-methylene-pentanoic acid ethyl ester in the form of a yellow oil.

3.70 g (15.1 mmol) of 5-ethoxy-2-formylamino-3-hydroxy-4-methylene-pentanoic acid ethyl ester are dissolved in 100 ml of 1,2-dichloroethane, and 1.8 ml (22.8 mmol) of thionyl bromide are added dropwise at room temperature. After one hour, 100 ml of water are added and the mixture is stirred vigorously for 15 minutes. The organic phase is separated off, washed in succession with 1N potassium hydrogen carbonate solution and with brine, dried over sodium sulfate, filtered and concentrated by evaporation. 5-ethoxy-4-bromomethyl-2-formylamino-pent-3-enoic acid ethyl ester is obtained in the form of a yellowish-brown oil which is reacted further in the crude state.

3.12 g (10.1 mmol) of 5-ethoxy-4-bromomethyl-2-formylamino-pent-3-enoic acid ethyl ester and 30 ml (118 mmol) of triisopropyl phosphite (90%) are heated to 80° C. and stirred under a pressure of approximately 130 mbar for 7 hours. The excess triisopropyl phosphite is distilled off and the residue is purified by chromatography on silica gel with methylene oxide/methanol (97:3 to 95:5). 5-ethoxy-4-dihydropropylphosphonomethyl-2-formylamino-pent-3-enoic acid ethyl ester is obtained in the form of a yellow oil.

EXAMPLE 20

5.4 g (12 mmol) of ethyl 8-acetoxy-diisopropylphosphonomethyl-2-formylamino-oct-3-enoate are dissolved in 40 ml of CH$_2$Cl$_2$. Then 6.2 ml (48 mmol) of trimethylbromosilane are added dropwise at room temperature to this solution. The reaction mixture is allowed to stand for 24 hours at room temperature and, after the dropwise addition of 40 ml of ethanol, allowed to stand for another 24 hours and then concentrated by evaporation. The residue is dissolved in 40 ml of ethanol, and a mixture of 40 ml of propylene oxide and 40 ml of ethanol is added dropwise to this solution. The suspension so obtained is stirred for 1 hour at room temperature and for 1 hour at 0° C., and then filtered with suction. The filter product is dried, giving of ethyl 2-amino-4-phosphonomethyl-8-hydroxy-oct-3-enoate. Melting point: from 233° C. (decomp.).

The starting material can be prepared a follows:

Hexanediol monoacetate is prepared substantially in accordance with the method described by H. Mattes and C. Benezara, J. Org. Chem. 53 (12), pp. 2732-7 (1988).

6-Acetoxyhexanal is prepared by the method described by K. Funakoshi et al., Chem. Pharm. Bull. 37 (8), pp. 1990-1994 (1989).

16 g (101.1 mmol) of 6-acetoxyhexanal, 9.2 g (113 mmol) of dimethylammonium chloride and 9.2 ml (118.3 mmol) of a 37% solution of formaldehyde are stirred for 1 hour at a bath temperature of 110° C. The mixture is allowed to cool and extracted three times with $CH_2Cl_2$. The combined organic phases are dried over $Na_2SO_4$, filtered, and concentrated by evaporation giving 6-acetoxy-2-methylene-hexanal as a slightly yellowish oil which is further reacted without purification.

450 mg of copper(I) oxide are added to a stirred solution of 15 (88 mmol) of 6-acetoxy-2-methylene-hexanal and 10.6 ml (97 mmol) of ethyl isocyanoacetate in 150 ml of toluene. After the exothermic reaction has subsided, the reaction mixture is stirred for 1 hour at room temperature and filtered over Hyflo ® (filter aid). The filtrate is concentrated by evaporation and the residue is taken up in 110 ml of tetrahydrofuran. After addition of 25 ml of water, the batch is refluxed for 4 hours and then concentrated by evaporation. The residue is taken up in toluene, and after concentrating once more the residue is chromatographed over silica gel with hexane/ethyl acetate (1:1) to give 8-acetoxy-2-formylamino-3-hydroxy-4-methylene-octanoic acid as a yellow oil.

10 g (33.2 mmol) of 8-acetoxy-2-formylamino-3-hydroxy-4-methylene-octanoic acid are dissolved in 100 ml of $CH_2Cl_2$. Then 3 ml (40 mmol) of thionyl bromide are added dropwise at room temperature. After 1 hour, 70 ml of water are added and the batch is stirred vigorously for 10 minutes. The organic phase is separted and washed once with water, once with a 1N solution of $KHCO_3$ and once with water. The aqueous phases are are extracted twice with $CH_2Cl_2$. The combined organic phases are dried over $Na_2SO_4$, filtered and concentrated by evaporation giving ethyl 8-acetoxy-4-bromomethyl-2-formylamino-oct-3-enoate as a yellow oil which is further reacted without purification.

11.5 g (31.5 mmol) of ethyl 8-acetoxy-4-bromomethyl-2-formylamino-oct-3-enoate and 34.6 ml (126.4 mmol) of triisopropyl phosphite (90%) are heated to 80° C. and stirred for 18 hours under a pressure of 100 mbar. Excess triisopropyl phosphite is removed by distillation and the residue is chromatographed over silica gel with ethyl acetate to give 8-acetoxy-4-diisopropylphosphonomethyl-2-formylamino-oct-3-enoate as a yellow oil.

In an analogous manner, 2-amino-10-hydroxy-4-phosphonomethyl-dec-3-enoic acid can be prepared.

EXAMPLE 21

2.4 g (5 mmol) of ethyl 7-ethoxycarbonylmethoxy-2-formylamino-4-diisopropylphonomethyl-hept-3-enoate are dissolved in 24 ml of $CH_2Cl_2$. Then 2.6 ml (20 mmol) of trimethylbromosilane are added dropwise at room temperature to this solution. The reaction mixture is allowed to stand for 24 hours at room temperature and, after the dropwise addition of 24 ml of ethanol, allowed to stand again for 24 hours. The reaction mixture is concentrated by evaporation and the residue is dissolved in 24 ml of ethanol. A mixture of 24 ml of propylene oxide and 24 ml of ethanol is then added dropwise to this solution. The suspension so obtained is stirred for 1 hour at 0° C. and then filtered with suction. The filter product is dried, giving 2-amino-7-ethoxycarbonylmethoxy-4-phosphonomethyl-hept-3-enoic acid with a melting point of 215°-218° C.

The starting material can be prepared as follows:

5-Benzyloxypentanol is prepared by a literature method: M. V. Sargent et al., J. Chem. Soc., Perkin Trans. I, pp. 131-132, 1990.

40 mg of copper powder are added to 10 g (51.4 mmol) of benzyloxy pentanol in 20 ml of cyclohexane. At reflux, a mixture of 5.9 ml (56.4 mmol) of ethyl diazoacetate and 50 ml of cyclohexane is added dropwise, whereupon evolution of $N_2$ ensues. The reaction mixture is refluxed for 3 hours and then stirred for 15 hours at room temperature. The reaction mixture is then filtered and concentrated by evaporation. The residue is chromatographed on silica gel with hexane/ethyl acetate (4:1) giving 5-ethoxycarbonylmethoxypentyl ether as a yellowish liquid.

58 g (0.21 mol) of benzyl 5-ethoxycarbonylmethoxypentyl ether are dissolved in 580 ml of tetrahydrofuran and the solution is hydrogenated under normal pressure at room temperature by addition of 5.8 g of 10% Pd/C as catalyst. Upon cessation of hydrogenation, the catalyst is removed by filtration and the filtrate is concentrated by evaporation. Distillation of the residue gives 5-ethoxycarbonylmethoxypentanol as a colourless liquid of b.p. 107°-111° C./$2.10^{-2}$ torr.

5-Ethoxycarbonylmethoxypentanal is prepared according to the literature from 5-ethoxycarbonylmethoxypentanol (EP 231 078)

16 g (85 mmol) of 5-ethoxycarbonylmethoxypentanal, 7.8 g (95.2 mmol) of dimethylammonium chloride and 7.4 ml (99.4 mmol) of a 37% solution of formaldehyde are stirred for 1 hour at a bath temperature of 110° C. The reaction mixture is allowed to cool and extracted three times with $CH_2Cl_2$. The combined organic phases are dried over $Na_2SO_4$, filtered and concentrated by evaporation giving ethyl 7-formyl-3-oxaoct-7-enoate as a colourless oil which is further reacted without purification.

450 mg of copper(I) oxide are added to a stirred mixture of 10.5 g (52.4 mmol) of ethyl 7-formyl-3-oxaoct-7-enoate and 6.3 ml (58 mmol) of ethyl isocyanoacetate in 100 ml of toluene, whereupon a rapid and vigorous exothermic reaction ensues. When the reaction has subsided, the reaction mixture is stirred for 1 hour at room temperature and filtered over Hyflo ®. The filtrate is concentrated by evaporation and the residue is taken up in 100 ml of tetrahydrofuran. After addition of 20 ml of water, the batch is stirred for 4 hours under reflux and concentrated by evaporation. The residue is taken up in toluene and the solution is concentrated by evaporation. The residue is chromatographed on silica gel with hexane/ethyl acetate (1:2) giving ethyl 7-ethoxycarbonylmethoxy-2-formylamino-3-hydroxy-4-methylene-heptanoate as a brown oil.

5 g (15.1 mmol) of ethyl 7-ethoxycarbonylmethoxy-2-formylamino-3-hydroxy-4-methylene-heptanoate are dissolved in 50 ml of $CH_2Cl_2$ and 1.4 ml (18.1 mmol) of thionyl bromide are added dropwise at room temperature. After 2 hours 50 ml of water are added and the batch is stirred vigorously for 10 minutes. The organic phase is separated and washed once with water, once with a 1N solution of KHCO$_3$ and twice with water. The aqueous phases are extracted once with CH$_2$Cl$_2$. The combined phases are dried over Na$_2$SO$_4$, filtered, and the filtrate is concentrated by evaporation giving ethyl 4-bromomethyl-7-ethoxycarbonylmethoxy-2-formylamino-hept-3-enoate as a yellow oil which is further reacted without purification. 6.4 g (15 mmol) of ethyl 4-bromomethyl-7-ethoxycarbonylmethoxy-2-formylamino-hept-3-enoate and 14.8 ml (60 mmol) of triisopropyl phosphite (90%) are heated to 80° C. and stirred for 18 hours under a pressure of 100 mbar. Excess triisopropyl phosphite is removed by distillation and the residue is chromatographed over silica gel with hexane/ethyl acetate (1:2:5%) to give ethyl 7-ethoxycarbonylmethoxy-2-formylamino-4-diisopropylphosphonomethyl-hept-3-enoate as a brown oil.

EXAMPLE 22

5.5 g (11.8 mmol) of ethyl 6-ethoxycarbonylmethoxy-2-formylamino-4-diisopropylphosphonomethyl-hex-3-enoate are dissolved in 55 ml of CH$_2$Cl$_2$ and 6.1 ml (42.3 mmol) of trimethylbromosilane are then added dropwise at room temperature to this solution. The reaction mixture is allowed to stand for 24 hours at room temperature and, after the dropwise addition of 55 ml of ethanol, allowed to stand for a further 24 hours. The reaction mixture is concentrated by evaporation, the residue is dissolved in 24 ml of ethanol, and a mixture of 55 ml of propylene oxide and 55 of ethanol is added dropwise to this solution. The suspension so obtained is stirred for 1 hour and then filtered with suction. The filter product is dried giving 2-amino-6-ethoxycarbonylmethoxy-4-phosphonomethyl-hex-3-enoic acid with a melting point of 213°-215° C. (decomp.) as a white oil.

The starting material may be prepared as follows:

Benzyl 4-hydroxybutyrate is prepared according to the literature: F. Dardoise et al., Tetrahedron Vol. 45, No. 24, pp. 7783-94, 1989.

65 g (0.33 mol) of benzyl 4-hydroxybutyrate and 260 mg of copper powder are charged to 120 ml of cyclohexane and the mixture is heated to reflux. Then a mixture of 38.7 ml (0.37 mol) of ethyl diazoacetate and 300 ml of cyclohexane are added, whereupon evolution of N$_2$ ensues. The reaction mixture is stirred for 4 hours under reflux and then for 4 hours at room temperature, filtered over a glass fibre filter and concentrated by evaporation. The residue is chromatographed on silica gel with hexane/ethyl acetate 4:1, giving benzyl 4-ethoxycarbonylmethoxybutyrate as a colourless liquid.

45 g (0.16 mol) of benzyl 4-ethoxycarbonylmethoxybutyrate 58 g are dissolved in 450 ml of tetrahydrofuran and the solution is hydrogenated under normal pressure at room temperature by addition of 4.5 g of 5% Pd/C. Upon cessation of hydrogenation, the catalyst is removed by filtration and the filtrate is concentrated by evaporation giving 4-ethoxycarbonylmethoxybutyric acid which is further reacted without purification.

36 g (0.19 mol) of 4-ethoxycarbonylmethoxybutyric acid are charged to 180 ml of toluene and 0.1 ml of dimethyl formamide is added. Then 24.4 ml (0.28 mol) of oxalyl chloride are added dropwise over 30 minutes. When the addition is complete, the reaction mixture is heated to 50° C., stirred for 1 hour and concentrated by evaporation. Distillation of the residue gives 4-ethoxycarbonylmethoxybutyric acid chloride as a clear colourless liquid of b.p. 87°-89° C./2.10$^{-2}$ torr.

29 g (0.14 mol) of 4-ethoxycarbonylmethoxybutyric acid chloride are dissolved in 290 ml of tetrahydrofuran and the solution is hydrogenated under normal pressure at 10°-15° C. by addition of 5.8 g of 5% Pd/C and 18 ml of 2,6-lutidine. Upon cessation of hydrogenation, the catalyst is removed by filtration and the filtrate is concentrated by evaporation. Distillation of the crude product gives 4-ethoxycarbonylmethoxybutanal as a clear colourless liquid of b.p. 72°-74° C./2.10$^{-2}$ torr.

11 g (63.1 mmol) of 4-ethoxycarbonylmethoxybutanal, 5.8 g (71.4 mmol) of dimethylammonium chloride and 5.5 ml (73.5 mmol) of a 37% solution of formaldehyde are stirred for 1 hour at a bath temperature of 110° C. The reaction mixture is allowed to cool and extracted three times with CH$_2$Cl$_2$ The combined organic phases are dried over Na$_2$SO$_4$ and concentrated by evaporation giving 4-ethoxycarbonylmethoxy-2-methylene-butanal as a yellowish liquid which is further reacted without purification.

490 mg of copper(I) oxide are added to a stirred mixture of 11 g (59.1 mmol) of 4-ethoxycarbonylmethoxybutanal and 7.2 ml (65.3 mmol) of ethyl isocyanoacetate in 100 ml of toluene are after the exothermic reaction has subsided, the reaction mixture is stirred for 1 hour at room temperature, filtered over Hyflo ® and concentrated by evaporation. The residue is taken up in 120 ml of tetrahydrofuran and 30 ml of water are added. The reaction mixture is stirred for 4 hours under reflux and concentrated by evaporation. The residue is taken up in toluene and the solution is concentrated by evaporation. The residue is chromatographed on silica gel with hexane/ethyl acetate (1:2), giving ethyl 6-ethoxycarbonylmethoxy-2-formylamino-3-hydroxy-4-methylene-hexanoate as a yellow oil.

7.5 g (23.6 mmol) of ethyl 6-ethoxycarbonylmethoxy-2-formylamino-3-hydroxy-4-methylene-hexanoate are dissolved in 75 ml of CH$_2$Cl$_2$ and 2.2 ml (28.3 mmol) of thionyl bromide are then added dropwise at room temperature to this solution. After 1 hour 50 ml of water are added and the reaction mixture is stirred vigorously for 10 minutes. The organic phase is separated and washed once with water, once with a 1N solution of KHCO$_3$ and once with brine. The aqueous phases are extracted twice with CH$_2$Cl$_2$. The combined organic phases are dried over Na$_2$SO$_4$, filtered, and concentrated by evaporation giving ethyl 4-bromomethyl-6-ethoxycarbonylmethoxy-2-formylamino-3-hydroxy-hexanoate as a yellow oil which is further reacted without purification.

9 g (23.7 mmol) of ethyl 4-bromomethyl-6-ethoxycarbonylmethoxy-2-formylamino-hex-3-enoate and 23.3 ml (94.8 mmol) of triisopropyl phosphite (90%) are heated to 80° C. and stirred for 18 hours under a pressure of 100 mbar. Excess triisopropyl phosphite is removed by distillation and the residue is chromatographed on silica gel with hexane/ethyl acetate 1:3 and then with hexane/ethyl acetate/ethanol (1:3:5%) giving ethyl 6-ethoxycarbonylmethoxy-2-formylamino-4-diisopropylphosphonomethyl-hex-3-enoate as a yellow oil.

EXAMPLE 23

11.5 g (26.4 mmol) of ethyl 6-acetoxy-2-formylamino-4-diisopropylphosphonomethyl-hept-3-enoate are dissolved in 70 ml of abs. CH$_2$Cl$_2$ and to this solution are added 13.7 ml (105.6 mmol) of trimethylbromosilane. The reaction mixture is allowed to stand for 24 hours at room temperature and, after addition of 70 ml of abs.

ethanol, allowed to stand again for 24 hours. The reaction mixture is concentrated by evaporation and the residue is dissolved in 70 ml of ethanol. A mixture of 70 ml of propylene oxide and 70 ml of ethanol is then added dropwise. The white suspension so obtained is stirred for 30 minutes at room temperature and for 30 minutes at 0° C. and then filtered with suction. The filter product is dried giving white crystals of ethyl 2-amino-6-hydroxy-4-phosphonomethyl-hept-3-enoate with a melting point of 211°–212° C. (decomp.).

The starting material may be prepared as follows:

Sodium 4-hydroxypentanoate is prepared substantially in accordance with the method described by J-J. Bourguignon et al., J. Med. Chem. 31 (5), 893–7, 1988.

80 g (0.57 mol) of sodium 4-hydroxypentanoate and 184.1 g (0.57 mol) of tetrabutylammonium bromide are suspended in 1.2 liters of abs. dimethyl formamide and the suspension is stirred for 15 minutes at room temperature. Then 67.8 ml (0.57 mol) of benzyl bromide are added dropwise and the reaction mixture is stirred for 15 hours at room temperature. The solution so obtained is diluted with water and extracted three times with ether. The organic phases are washed once with water and once with brine. The combined organic phases are dried over $MgSO_4$, filtered and concentrated by evaporation. Distillation of the residue gives 63.1 g of benzyl 4-hydroxypentanoate of b.p. 139°–140° C./$2.10^{-2}$ torr as a colourless oil.

63 g (302.5 mmol) of benzyl 4-hydroxypentanoate and 46.4 ml (332.8 mmol) of triethylamine are charged under nitrogen at room temperature to 300 ml of $CH_2Cl_2$. The mixture is cooled to 0° C. and 21.5 ml (302.5 mmol) of acetyl chloride are added dropwise at 0°–5° C. When the dropwise addition is complete, the ice bath is removed and stirring is continued overnight at room temperature. The reaction mixture is mixed with ice-water and the organic phase is separated and washed twice with water. The aqueous phases are extracted twice with $CH_2Cl_2$. The organic phases are combined, dried over $MgSO_4$, filtered and concentrated by evaporation. Distillation of the residue gives benzyl 4-acetoxypentanoate as a colourless oil of b.p. 126°–127° C./$2.10^{-2}$ torr.

87.5 g (0.35 mol) of benzyl 4-acetoxypentanoate are dissolved in 900 ml of abs. ethanol and the solution is hydrogenated at room temperature under normal pressure with the addition of 5 g of 10% Pd/C as catalyst. Upon cessation of hydrogenation, the catalyst is removed by filtration and the filtrate is concentrated by evaporation. Distillation of the residue gives 4-acetoxypentanoic acid as a colourless oil of b.p. 110°–112° C./$2.10^{-2}$ torr.

46.5 g (0.29 mol) of 4-acetoxypentanoic acid are dissolved at room temperature in 230 ml of abs. toluene, and then 0.2 ml of abs. Dimethyl formamide is added. Then 32.6 ml (0.38 mol) of oxalyl chloride are added dropwise such that the evolution of gas remains under control. When the dropwise addition is complete, the reaction mixture is heated to 50° C. and stirred for 1 hour at this temperature. The orange-red reaction solution is concentrated by evaporation. Distillation of the residue gives 42.2 g of 4-acetoxypentanoic acid chloride as a colorless liquid of b.p.$_{34}$ 110°–112° C.

45.0 g (0.25 mol) of 4-acetoxypentanoic acid chloride are dissolved in 450 ml of abs. tetrahydrofuran. Then 31.9 ml (0.27 mol) of 2,6-lutidine and 9 g of 5% Pd/C are added and hydrogenation is carried out for 1 hour at 10°–15° C. Upon cessation of hydrogenation, the catalyst and the 2,6-lutidine are removed by filtration and the filtrate is concentrated by evaporation. Distillation of the residue gives 4-acetoxypentanal as a colourless liquid of b.p.$_{34}$ 98°–100° C.

18.0 g (124.8 mmol) of 4-acetoxypentanal, 11.5 g (140.7 mmol) of dimethylammonium chloride and 11.0 ml (146 mmol) of a 37% solution of formaldehyde are stirred for 1 hour at a bath temperature of 110° C. The reaction mixture is allowed to cool and then extracted three times with $CH_2Cl_2$. The combined organic phases are dried over $MgSO_4$, filtered and concentrated by evaporation, giving 18.3 g of 4-acetoxy-2-methylene-pentanal as a colourless oil which is further reacted without purification.

18.0 g (115.2 mmol) of 4-acetoxy-2-methylene-pentanal and 15.4 ml (126.8 mmol) of ethyl isocyanoacetate are charged at room temperature to 130 ml of abs. toluene and 500 mg of copper(I) oxide are added, whereupon a rapid and vigorous exothermic reaction ensues. When the exothermic reaction has subsided, the reaction mixture is stirred for 1 hour at room temperature, filtered over Hyflo ® and concentrated by evaporation. The residue is taken up in 100 ml of tetrahydrofuran and 30 ml of water are added. The reaction mixture is refluxed for 4 hours and then concentrated by evaporation. The residue is taken up in toluene, and the solution is concentrated. The residue is chromatographed on silica gel with ethyl acetate/hexane (2:1), giving ethyl 6-acetoxy-2-formylamino-3-hydroxy-4-methylene-heptanoate as a brown oil.

17.0 g (59.1 mmol) of ethyl 6-acetoxy-2-formylamino-3-hydroxy-4-methylene-heptanoate are dissolved in 170 ml of $CH_2Cl_2$ and 5.5 ml (71 mmol) of thionyl bromide are then added dropwise at room temperature. After 1 hour, 100 ml of water are added and the batch is vigorously stirred for 10 minutes. The organic phase is separated and washed once with water, once with a 1N solution of $KHCO_3$ and twice with water. The aqueous phases are extracted twice with $CH_2Cl_2$. The combined organic phases are dried over $MgSO_4$, filtered and concentrated by evaporation, giving ethyl 6-acetoxy-4-bromomethyl-2-formylamino-hept-3-enoate as a brown oil which is further reacted without purification.

18.0 g (51.4 mmol) of ethyl 6-acetoxy-4-bromomethyl-2-formylamino-hept-3-enoate and 56.3 ml (205.6 mmol) of 90% triisopropyl phosphite are heated to 80° C. and the mixture is stirred for 18 hours under a pressure of 100–150 mbar. Excess triisopropyl phosphite is removed by distillation and the residue is purified by chromatography on silica gel with ethyl acetate/isopropanol (7:2), giving ethyl 6-acetoxy-2-formylamino-4-diisopropylphosphonomethyl-hept-3-enoate as an orange oil. yield.

EXAMPLE 24

2.5 g (8.89 mmol) of ethyl 2-amino-6-hydroxy-4-phosphonomethyl-hept-3-enoate are dissolved in 17 ml of $H_2O$ and the solution is heated to reflux. The reaction solution is kept for 12 hours at reflux temperature. The reaction solution is then treated with 0.3 g of activated carbon, stirred for 10 minutes and filtered over Hyflo ®. The filtrate is concentrated by evaporation and the residue is crystallised from water/ethanol and dried, giving white crystals of 2-amino-6-hydroxy-4-phosphonomethyl-hept-3-enoic acid. Melting point: 210° C. (decomp.).

EXAMPLE 25

12.7 g (30.2 mmol) of ethyl 6-acetoxy-2(R)-formylamino-4-diisopropylphosphonomethyl-hex-3-enoate are dissolved in 100 ml of abs. $CH_2Cl_2$ and 15.6 ml (120.8 mmol) of trimethylbromosilane are added to this solution at room temperature. The reaction mixture is allowed to stand for 24 hours at room temperature. After addition of 100 ml of abs. ethanol the reaction mixture is again allowed to stand for 24 hours at room temperature and then concentrated by evaporation. The residue is dissolved in ethanol and then a mixture of 100 ml of propylene oxide and 100 ml of ethanol is added dropwise. The suspension so obtained is stirred for 1 hour at 0° C. and then filtered with suction. The filter product is stirred overnight in ether and again filtered with suction. The filter product is dried, giving white crystals of 2(R)-amino-6-hydroxy-4-phosphonomethyl-hex-3-enoic acid. Melting point: 170° C. (decomp.). ee=92%; $\alpha_D = -45.6° \pm 1°$ (c=1.0 $H_2O$).

The starting material can be prepared as follows:

23.2 g (84.9 mmol) of ethyl 6-acetoxy-2(R)-formylamino-4-methylene-hex-3-enoate (ZR configuration) are dissolved in 250 ml of abs. $CH_2Cl_2$ and 7.9 ml (101.9 mmol) of thionyl bromide are added to this solution at room temperature. After 2 hours, 200 ml of water are added and the reaction mixture is stirred vigorously for 10 minutes. The organic phase is separated and washed once with water, once with a 1N solution of $KHCO_3$ and twice with water. The aqueous phases are extracted twice with $CH_2Cl_2$. The combined organic phases are dried over $MgSO_4$, filtered and concentrated by evaporation, giving ethyl 6-acetoxy-4-bromomethyl-2(R)-formylamino-hex-3-enoate as a brown oil which is further reacted without purification.

21.2 g (63.1 mmol) of ethyl 6-acetoxy-4-bromomethyl-2(R)-formylamino-hex-3-enoate and 69.1 ml (252.2 mmol) of 90% triisopropyl phosphite are heated to 80° C. and the mixture is stirred for 18 hours under a pressure of 100–150 mbar. Excess triisopropyl phosphite is removed by distillation and the residue is purified by flash chromatography on silica gel with ethyl acetate/ethanol (19:1), giving 8.6 g of ethyl 6-acetoxy-2(R)-formylamino-4-diisopropylphosphonomethyl-hex-3-enoate a yellowish-orange oil. ee=92.5%; $\alpha_D$−90.2°±0.4° (c=2.84 $CH_2Cl_2$).

EXAMPLE 26

1.75 g (3.6 mmol) of benzyl 6-acetoxy-2-formylamino-4-diisopropylphosphonomethyl-hex-3-enoate are dissolved in 15 ml of $CH_2Cl_2$. Then 1.88 ml (14.5 mmol) of trimethylbromosilane are added to this solution at room temperature. The reaction mixture is allowed to stand for 24 hours at room temperature. After addition of 15 ml of benzyl alcohol the reaction mixture is allowed to stand for 48 hours at room temperature and then concentrated by evaporation at 70° C. under a high vacuum. The residue is dissolved in 15 ml of ethanol and then a mixture of 15 ml of propylene oxide and 15 ml of ethanol is added dropwise to this solution. The suspension so obtained is stirred for 30 minutes in an ice bath and then filtered with suction. The crystals so obtained are recrystallised hot from ethanol/water and dried, giving white crystals of benzyl 6-acetoxy-2-amino-4-phosphonomethyl-hex-3-enoate. Melting point: 204°-205° C. (decomp.).

The starting material can be obtained as follows:

12 g (84.1 mmol) of 4-acetoxy-2-methylen-butanal and 16.2 g (92.5 mmol) of benzyl cyanoacetate are charged at room temperature to 100 ml of abs. toluene and 450 mg of copper(I) oxide are added, whereupon a rapid and vigorous exothermic reaction ensues after gentle heating. When the exothermic reaction has subsided, the reaction mixture is stirred for 2 hours at room temperature, filtered over Hyflo® and concentrated by evaporation. The residue is taken up in 80 ml of tetrahydrofuran, 20 ml of water are added, and the batch is refluxed for 4 hours. The batch is concentrated by evaporation and the residue is taken up in toluene. The solution is concentrated by evaporation and the residue is chromatographed on silica gel with ethyl acetate/hexane (2:1), giving benzyl 6-acetoxy-2-formylamino-3-hydroxy-4-methylene-hexanoate as an orange-red oil.

10.5 g (31.3 mmol) of benzyl 6-acetoxy-2-formylamino-3-hydroxy-4-methylenehexanoate are dissolved in 100 ml of abs. $CH_2Cl_2$. Then 2.91 ml (37.6 mmol) of thionyl bromide are added to this solution at room temperature. After 2 hours, 80 ml of water are added and the mixture is stirred vigorously for 10 minutes. The organic phase is separated and washed once with water, once with a 1N solution of $KHCO_3$ and twice with water. The aqueous phases are extracted twice with $CH_2Cl_2$. The combined organic phases are dried over $MgSO_4$, filtered and concentrated by evaporation, giving benzyl 6-acetoxy-4-bromomethyl-2-formylamino-hex-3-enoate as a yellowish-brown oil which is further reacted without purification.

11.1 g (27.9 mmol) of benzyl 6-acetoxy-4-bromomethyl-2-formylamino-hex-3-enoate and 30.5 ml (111.5 mmol) of 90% triisopropyl phosphite are heated to 80° C. and the mixture is stirred for 18 hours under a pressure of 100–150 mbar. Excess triisopropyl phosphite is removed by distillation and the residue is purified by chromatography over silica gel with ethyl acetate/isopropanol (7:1), giving benzyl 6-acetoxy-2-formylamino-4-diisopropylphosphonomethyl-hex-3-enoate as an orange oil.

EXAMPLE 27

Tablets, each containing 50 mg of 2-amino-6-hydroxy-4-phosphonomethyl-hex-3-enoic acid or a salt, for example the sodium salt, thereof, can be prepared as follows:

| Composition (10,000 tablets) | |
| --- | --- |
| active ingredient | 500.0 g |
| lactose | 500.0 g |
| potato starch | 352.0 g |
| gelatin | 8.0 g |
| talcum | 60.0 g |
| magnesium stearate | 10.0 g |
| silica (highly disperse) | 20.0 g |
| ethanol | q.s. |

The active ingredient is mixed with the lactose and 292 g of potato starch, and the mixture is moistened with an ethanolic solution of the gelatin and granulated through a sieve. After drying, the remaining potato starch, the magnesium stearate, the talcum and the silica are mixed in and the mixture is compressed to form tablets which each weigh 145.0 mg and contain 50.0 mg of active ingredient, and which may, if desired, be provided with dividing notches for finer adaptation of the dose.

EXAMPLE 28

Coated tablets, each containing 100 mg of 2-amino-6-hydroxy-4-phosphonomethyl-hex-3-enoic acid or a salt, for example the sodium salt, thereof, can be prepared as follows:

| Composition (for 1,000 coated tablets) | |
|---|---|
| active ingredient | 100.0 g |
| lactose | 100.0 g |
| corn starch | 70.0 g |
| talcum | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of the corn starch and water (with heating), and granulated. The granulate is dried, the remaining corn starch, the talcum and the calcium stearate are added and mixed with the granulate. The mixture is compressed to form tablets (weight: 280 mg), which are coated with a solution of the hydroxypropylmethylcellulose and the shellac in methylene chloride. Final weight of the coated tablet: 283 mg.

EXAMPLE 29

Gelatin dry-filled capsules, containing 100 mg of active ingredient, for example 2-amino-6-hydroxy-4-phosphonomethyl-hex-3-enoic acid or a salt, for example the sodium salt, thereof, can be prepared, for example, as follows:

| Composition (for 1,000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are intimately mixed. Then, first the lactose is added through a sieve having a mesh size of 0.6 mm and then the microcrystalline cellulose through a sieve having a mesh size of 0.9 mm. The mixture is again intimately mixed for 10 minutes. Finally, the magnesium stearate is added through a sieve having a mesh size of 0.8 mm. After further mixing for 3 minutes, size 0 gelatin dry-fill capsules are each filled with 390 mg of the resulting formulation

EXAMPLE 30

A 0.2% injection or infusion solution of 2-amino-6-hydroxy-4-phosphonomethyl-hex-3-enoic acid or of a salt, for example the sodium salt, thereof can be prepared, for example, as follows:

| Composition (for 1,000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a micro-filter. The buffer solution is added, and the mixture is made up to 2500 ml with water. To prepare dosage unit forms, 1.0 or 2.5 ml are introduced into each glass ampoule, which then contains 2.0 or 5.0 mg, respectively, of active ingredient.

EXAMPLE 31

In a manner analogous to that described in Examples 1 to 10 also the following compound can be manufactured:

2-amino-8-hydroxy-4-phosphonomethyl-oct-3-enoic acid ethyl ester, m.p. 230°–233° (decomp.);

2-amino-6-hydroxy-5-hydroxymethyl-4-phosphonomethyl-hex-3-enoic acid ethyl ester, m.p. 177°–180°, and 2-amino-10-hydroxy-4-phosphonomethyl-dec-3-enoic acid ethyl ester, m.p. 243°–244° (decomp.).

EXAMPLE 32

In a manner analogous to that described in Examples 27 to 30, it is also possible to prepare pharmaceutical preparations containing a different compound of formula I according to any one of Examples 1 to 26 and 31.

What is claimed is:

1. A compound of formula I,

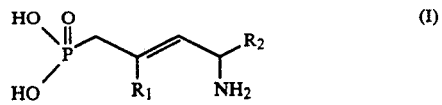

wherein $R_1$ is lower alkanoyloxy-lower alkyl or benzoyloxy-lower alkyl, lower alkoxy-lower alkyl or phenyl-lower alkoxy-lower alkyl, 6-aminohexyl, lower alkyl 6-aminohexyl or di-lower alkyl 6-aminohexyl and $R_2$ is carboxy, lower alkoxycarbonyl, 4- up to and including 7-membered cycloalkoxycarbonyl or phenyl-lower alkoxycarbonyl, any phenyl radicals in $R_1$ and/or $R_2$ being unsubstituted or mono-, di- or tri-substituted by lower alkyl, lower alkoxy, halogen, cyano and/or by trifluoromethyl, or a salt thereof.

2. A compound according to claim 1 of formula I, wherein $R_1$ is (a) $C_2$–$C_7$alkanoyloxy-$C_1$–$C_7$alkyl, (b) benzoyloxy-$C_1$–$C_7$alkyl that is unsubstituted or mono- or di-substituted in the phenyl moiety by $C_1$–$C_4$alkyl, $C_1$–$C_4$alkoxy, halogen having an atomic number of up to and including 35, cyano and/or by trifluoromethyl, (c) $C_1$–$C_4$alkoxy-$C_1$–$C_7$alkyl, (d) a phenyl-$C_1$–$C_4$alkoxy-$C_1$–$C_7$alkyl group that is unsubstituted or mono- or di-substituted in the phenyl moiety by $C_1$–$C_4$alkyl, $C_1$–$C_4$alkoxy, halogen having an atomic number of up to and including 35, cyano and/or by trifluoromethyl, or (e) 6-aminohexyl, $C_1$–$C_4$alkyl 6-aminohexyl or di-$C_1$–$C_7$alkyl 6-aminohexyl, and $R_2$ is carboxy, $C_1$–$C_4$alkoxycarbonyl, 5- to 7-membered cycloalkoxycarbonyl or phenyl-$C_1$–$C_4$alkoxycarbonyl that is unsubstituted or mono- or di-substituted by $C_1$–$C_4$alkyl, $C_1$–$C_4$alkoxy, halogen having an atomic number of up to and including 35, cyano and/or by trifluoromethyl, or a salt thereof.

3. A compound according to claim 1 of formula I, wherein $R_1$ is (a) benzoyloxy-$C_1$–$C_7$ alkyl that is unsubstituted or mono- or di-substituted in the phenyl moiety by $C_1$–$C_4$alkyl, $C_1$–$C_4$alkoxy, halogen having an atomic number of up to and including 35, cyano and/or by trifluoromethyl, (b) phenyl-$C_1$-$C_4$alkoxy-$C_1$-$C_7$alkyl that is unsubstituted or mono- or di-substituted in the phenyl moiety by $C_1$-$C_4$alkyl, $C_1$-$C_4$alkoxy, halogen having an atomic number of up to and including 35, cyano and/or by trifluoromethyl, or (c) amino-6-aminohexyl, and $R_2$ is carboxy, $C_1$-$C_4$alkoxycarbonyl or phenyl-$C_1$-$C_4$alkoxycarbonyl that is unsubstituted or mono- or di-substituted by $C_1$-$C_4$alkyl, $C_1$-$C_4$alkoxy, halogen having an atomic number of up to and including 35, cyano and/or by trifluoromethyl, or a salt thereof.

4. A compound according to claim 1 of formula I, wherein $R_1$ is $C_1$-$C_4$alkoxy-$C_1$-$C_7$alkyl, benzoyloxy-$C_1$-$C_4$alkyl or 6-aminohexyl, and $R_2$ is carboxy or $C_1$-$C_4$-alkoxycarbonyl, or a salt thereof.

5. A compound according to claim 1 of formula I, wherein $R_1$ is methoxymethyl, ethoxymethyl, 2-methoxyethyl, 2-benzoyloxyethyl, benzyloxymethyl, 2-benzyloxyethyl, or 6-aminohexyl, and $R_2$ is carboxy or $C_1$-$C_4$alkoxycarbonyl, or a salt thereof.

6. A compound according to claim 1 of formula I, wherein $R_1$ is 6-aminohexyl, and $R_2$ is carboxy or $C_1$-$C_4$alkoxycarbonyl, or a salt thereof.

7. A compound according to claim 1 of formula I, wherein $R_1$ is $C_1$-$C_4$alkoxy-$C_1$-$C_4$ alkyl, phenyl-$C_1$-$C_4$alkoxy-$C_1$-$C_4$-alkyl, or benzoyloxy-$C_1$-$C_4$alkyl, and $R_2$ is carboxy or $C_1$-$C_4$alkoxycarbonyl, or a salt thereof.

8. A compound according to claim 1 of formula I, wherein $R_1$ is $C_1$-$C_4$alkoxy-$C_2$-$C_4$alkyl, and $R_2$ is carboxy, $C_1$-$C_4$alkoxycarbonyl or a phenyl-$C_1$-$C_4$alkoxycarbonyl group that is unsubstituted or mono- or di-substituted by $C_1$-$C_4$alkyl, $C_1$-$C_4$alkoxy, halogen having an atomic number of up to and including 35, cyano and/or by trifluoromethyl, or a salt thereof.

9. A compound according to claim 1 selected from the group consisting of,
2-amino-6-methoxy-4-phosphonomethyl-hex-3-enoic acid ethyl ester,
2-amino-6-methoxy-4-phosphonomethyl-hex-3-enoic acid,
2,10-diamino-4-phosphonomethyl-dec-3-enoic acid,
2,10-diamino-4-phosphonomethyl-dec-3-enoic acid ethyl ester,
2-amino-5-benzyloxy-4-phosphonomethyl-pent-3-enoic acid ethyl ester,
5-ethoxy-2-amino-4-phosphonomethyl-penten-3-oic acid ethyl ester,
2-amino-7-ethoxycarbonylmethoxy-4-phosphonomethyl-hept-3-enoic acid,
2-amino-6-ethoxycarbonylmethoxy-4-phosphonomethyl-hex-3-enoic acid, and
benzyl 6-acetoxy-2-amino-4-phosphonomethyl-hex-3-enoate,
or a pharmaceutically acceptable salt thereof.

10. A pharmaceutical preparation containing an amount therapeutically effective in the treatment of epilepsy, ischaemia or migraine of a compound according to claim 1 in the free form or in the form of a pharmaceutically acceptable salt in admixture with pharmaceutically acceptable auxiliaries.

11. Method for the treatment of epilepsy, ischaemia and/or migraine, comprising administering a therapeutically effective amount of a compound according to claim 1 to a warm-blooded organism in need of such treatment.

* * * * *

UNITED STATES PATENT AND TRADEMARK OFFICE
CERTIFICATE OF CORRECTION

PATENT NO. : 5,294,734
DATED : March 15, 1994
INVENTOR(S) : Angst et al.

It is certified that error appears in the above-identified patent and that said Letters Patent is hereby corrected as shown below:

Column 43, line 5, after "(c)" please delete "amino-6-" and insert --6- -- in lieu thereof.

Signed and Sealed this

Sixteenth Day of August, 1994

Attest:

BRUCE LEHMAN

Attesting Officer     Commissioner of Patents and Trademarks